(12) United States Patent
Wang et al.

(10) Patent No.: US 6,996,550 B2
(45) Date of Patent: Feb. 7, 2006

(54) METHODS AND APPARATUS FOR PREPARING HIGH-DIMENSIONAL COMBINATORIAL EXPERIMENTS

(75) Inventors: Youqi Wang, Atherton, CA (US); Marco Falcioni, San Francisco, CA (US); Stephen J. Turner, San Jose, CA (US); C. Eric Ramberg, San Jose, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 750 days.

(21) Appl. No.: 10/024,649

(22) Filed: Dec. 17, 2001

(65) Prior Publication Data

US 2002/0152057 A1 Oct. 17, 2002

Related U.S. Application Data

(60) Provisional application No. 60/256,270, filed on Dec. 15, 2000.

(51) Int. Cl.
*G06F 15/18* (2006.01)

(52) U.S. Cl. ........................................................ 706/19
(58) Field of Classification Search ................... 706/19
See application file for complete search history.

(56) References Cited

U.S. PATENT DOCUMENTS

| 4,368,509 A | 1/1983 | Li ............................. 364/148 |
| 4,472,770 A | 9/1984 | Li ............................. 364/148 |
| 4,710,864 A | 12/1987 | Li ............................. 364/148 |
| 5,143,854 A | 9/1992 | Pirrung et al. |
| 5,331,573 A | 7/1994 | Balaji et al. ................. 364/500 |
| 5,356,756 A | 10/1994 | Cavicchi et al. ............. 430/315 |
| 5,386,507 A | 1/1995 | Teig et al. ................... 395/161 |
| 5,434,796 A | 7/1995 | Weininger ................... 364/496 |

(Continued)

FOREIGN PATENT DOCUMENTS

| WO | WO 96/11878 | 4/1996 |
| WO | WO 99/59722 | 11/1999 |
| WO | WO 00/23921 | 4/2000 |
| WO | WO 02/04112 | 1/2002 |

OTHER PUBLICATIONS

James N. Cawse, Ph.D., "Experimental Strategies for Combinatorial and High–Throughput Materials Development", Accounts of Chemical Research, 2001, vol. 34, No. 3, pp. 213–221.

L. A. Corkan et al., "Application of an Automated Chemistry Workstation to Problems in Synthetic Chemistry", Chemometrics and Intelligent Laboratory Systems: Lab. Info. Mgmt., 1992, vol. 17, pp. 95–105.

(Continued)

*Primary Examiner*—George Davis

(57) ABSTRACT

Computer-implemented methods, systems and apparatus, including computer program apparatus, provide techniques for designing a set of experiments to be performed with a set of resources. A plurality of experimental configurations are generated based on a set of parameters describing factors to be varied in the experiments and a set of constraints representing limitations on operations that can be performed with the set of resources. A set of experiments is defined based on a selected configuration. The constraints can be represented as patterns defining an application of a parameter to a set of one or more points of an experimental lattice.

95 Claims, 11 Drawing Sheets

U.S. PATENT DOCUMENTS

| | | | |
|---|---|---|---|
| 5,526,281 A | 6/1996 | Chapman et al. | 364/496 |
| 5,571,639 A | 11/1996 | Hubbell et al. | |
| 5,759,779 A | 6/1998 | Dehlinger | 435/436 |
| 5,763,263 A | 6/1998 | Dehlinger | 435/287 |
| 5,854,992 A | 12/1998 | Shakhnovich et al. | 702/27 |
| 5,862,514 A | 1/1999 | Huse et al. | 702/22 |
| 5,914,891 A | 6/1999 | McAdams et al. | 364/578 |
| 5,930,154 A | 7/1999 | Thalhammer-Reyero | 364/578 |
| 5,959,297 A | 9/1999 | Weinberg et al. | 250/288 |
| 5,980,096 A | 11/1999 | Thalhammer-Reyero | 364/578 |
| 6,004,617 A | 12/1999 | Schultz et al. | 427/8 |
| 6,030,917 A | 2/2000 | Weinberg et al. | 502/104 |
| 6,034,775 A | 3/2000 | McFarland et al. | 356/364 |
| 6,044,212 A | 3/2000 | Flavin et al. | 395/500.27 |
| 6,045,671 A | 4/2000 | Wu et al. | 204/298.11 |
| 6,081,766 A | 6/2000 | Chapman et al. | 702/27 |
| 6,144,897 A | 11/2000 | Selliers | 700/269 |
| 6,175,816 B1 | 1/2001 | Flavin et al. | 703/13 |
| 6,187,164 B1 | 2/2001 | Warren et al. | 205/81 |
| 6,188,965 B1 | 2/2001 | Mayo et al. | 702/27 |
| 6,295,539 B1 * | 9/2001 | Isip, Jr. | 707/201 |
| 6,411,945 B1 | 6/2002 | Nakajima | 706/19 |
| 6,507,945 B1 | 1/2003 | Rust et al. | 717/103 |
| 6,618,852 B1 | 9/2003 | van Eikeren et al. | 717/108 |
| 6,640,191 B1 | 10/2003 | Deem et al. | 702/19 |

OTHER PUBLICATIONS

L. A. Corkan and J. S. Lindsey, "Design Concepts for Synthetic Chemistry Workstations", Advances in Laboratory Automation Robotics, 1990, vol. 6, pp. 447–497.

L. A. Corkan and J. S. Lindsey, "Experiment Manager Software for an Automated Chemistry Workstation, Including a Scheduler for Parallel Experimentation", Chemometrics and Intelligent Laboratory Systems; Lab. Info. Mgmt., 1992, vol. 17, pp. 47–47.

M. W. Deem, "A Statistical Mechanical Approach to Combinatorial Chemistry", Advances in Chemical Engineering 28, Academic Press, 2001, pp. 81–121.

M. Falcioni and M. W. Deem, "Library Design in Combinatorial Chemistry by Monte Carlo Methods", Phys. Rev. E 61, 2000, pp. 5948–5952.

S. P.A. Foder, J. Leighton Red, M. C. Pirrung, L. Stryer, A. T. Lu, D. Solas, "Light–directed, spatially addressable parallel chemical synthesis", Science, (1991) vol. 251, pp. 767–773.

R. A. Houghten "Parallel array and mixture–based synthetic combinatorial chemistry: tools for the next millennium", Annu. Rev. Pharmocol. Toxicol. (2000) vol. 40, pp. 273–282.

H. Koinuma, T. Koida, T. Ohnishi, D. Komiyama, M. Lippmaa, M. Kawasaki, "Parallel fabrication of artificially designed superlattices by combinatorial laser MBE", Appl. Phys. A 69 Supp., (1999) S29–S31.

J. S. Lindsey, "Automated Workstations for Chemical Synthesis in Japan: A New Paradigm for Pharmaceutical Research", Am. Lab., 1993, pp. 17, 18. 20.

J. S. Lindsey, "A Retrospective on the Automation of Laboratory Synthetic Chemistry", Chemometrics and Intelligent Laboratory Systems: Lab. Inf. Mgmt., 1992, vol. 17, pp. 15–45.

J. S. Lindsey and L. A. Corkan, "Toward High–Performance Parallel Experimentation Machines: Use of a Scheduler as a Quantitative Computer–Aided Design Tool for Evaluating Workstation Performance", Chemometrics and Intelligent Laboratory Systems: Lab. Info. Mgmt., 1993, vol. 21, pp. 139–150.

A. M. Thayer, "Bioinformatics for the Masses", Business, 2000, vol. 78, No. 6, CENEAR 78, pp. 19–32.

SAS Institute, "JMP Statistical Discovery Software: Design of Experiments", 2000, Version 4.

B. Yan, L. Liu, C. A. Astor and Q. Tang, "Determination of the absolute amount of resin–bound hydroxyl or carbonyl groups for the optimization of solid–phase combinatorial and parallel organic synthesis", Anal. Chem. (1999) vol. 71, pp. 4564–4571.

Manfred Baerns, et al. "Chemical Reaction Technology", 1987, Georg Thieme Verlag, Stuttgart and New York, Textbook of Technical Chemistry, vol. 1.

J.J. Hanak, "The "Multiple–Sample Concept" in Materials Research: Synthesis, Compositional Analysis and Testing of Entire Multicomponent Systems", © 1970 Chapman and Hall Ltd., pp. 964–971.

Eric W. McFarland and W. Henry Weinberg, "Approaches for Rapid Materials Discovery Using Combinatorial Methods", 1998, Mat. Tech. vol. 13.3, pp. 107–120.

MODDE 4.0, "Graphical Software for Design of Experiments", © 1992–1997 Umetri AB, pp. 1–1 to 14–2.

Statistica vol. IV: Industrial Statistics, Copyright © StatSoft, 1995, pp. 4177–4473.

Peter G. Schultz and Xiao–Dong Xiang, "Combinatorial approaches to materials science", 1998, © Current Chemistry ISSN 1359–0286, pp. 153–158.

Linda C. Hsieh–Wilson, et al., "Lessons from the Immune System: From Catalysis to Materials Science", © 1996 American Chemical Society, vol. 29, pp. 164–170.

X.D. Xiang et al., "A Combinatorial Approach to Materials Discovery", Jun. 23, 1995, Science, vol. 268, pp. 1738–1740.

X.–D. Xiang and P.G. Schultz, "The Combinatorial Synthesis and Evaluation of Functional Materials", 1997 Physica C, vol. 282, pp. 428–430.

Earl Danielson, et al., "A combinatorial approach to the discovery and optimization of luminescent materials", Oct. 30, 1997, Nature, vol. 389, No. 30, pp. 944–948.

Xiao–Dong Sun, "Solution–Phase Synthesis of Luminescent Materials Libraries", 1997, Advanced Materials, vol. 9, pp. 1046–1049.

Kagaku, "Combinatorial Chemistry: Inconceivable without Computers", Combinatorial Chemistry, vol. 51, No. 8, pp. 480–483 & 583 (1996). Original Japanese reference and English translation included.

Yamagata et al., "Constructing an Assay System with HTS", IV High Throughput Screening, pp. 179–191 (1997). Original Japanese reference and English translation included.

H.–D. Klein, "Statistische Verschusplanung", 1995, Nachr. Chem. Tech. Lab. vol. 43, pp. 1078, 1080–1082 (with English translation).

Briceno et al., SCIENCE 270, pp. 273–275, 1995.

Thayer, Chem. Eng. News, Feb. 12, 1996 pp. 57–64.

Danielson et al., SCIENCE 279, pp. 837–839, 1998.

Maier, "Combinatorial Chemistry—Challenge and Chance for the Development of New Catalysts and Materials," Angew. Chem. Int. Ed., 1999,38, 1216.

Michalewicz, "Genetic Algorithms + Data Structures = Evolution Programs," 3rd Ed., Springer, Berlin, Germany, 1996.

* cited by examiner

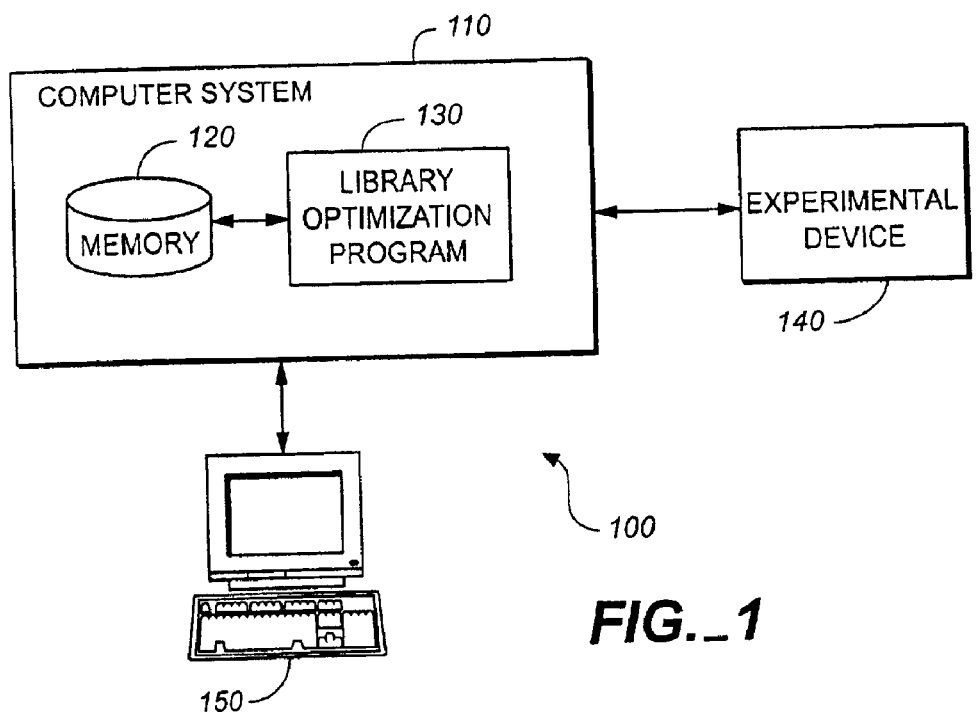
FIG._1
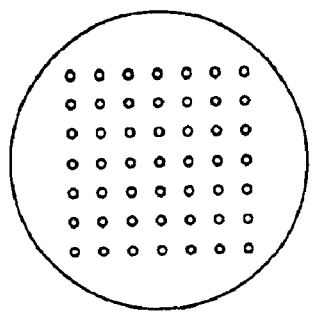
FIG._2A
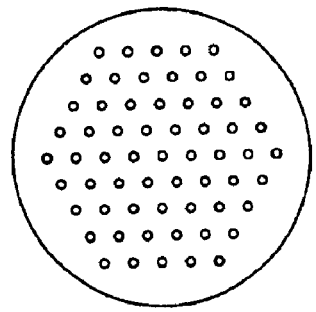
FIG._2B

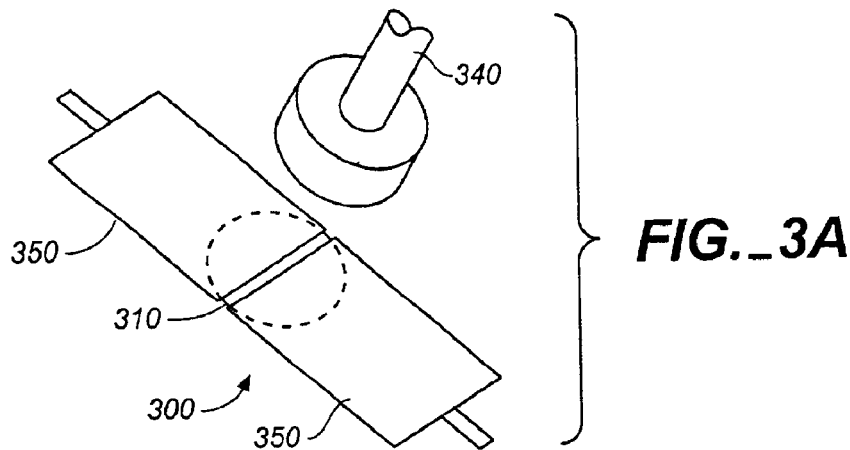
FIG._3A
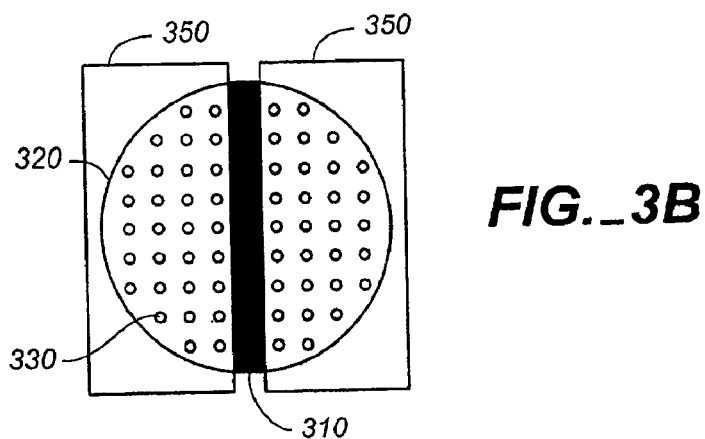
FIG._3B
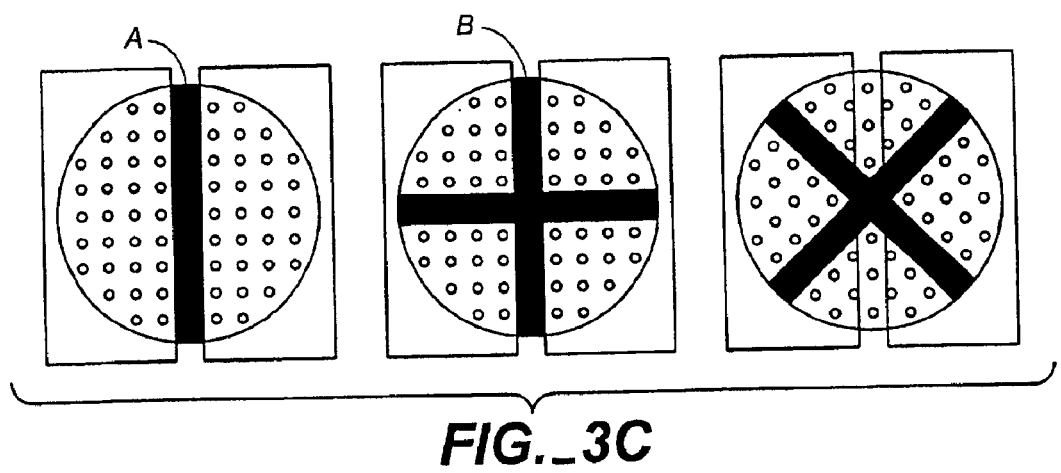
FIG._3C

FIG._4A
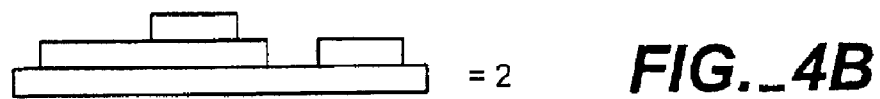
FIG._4B
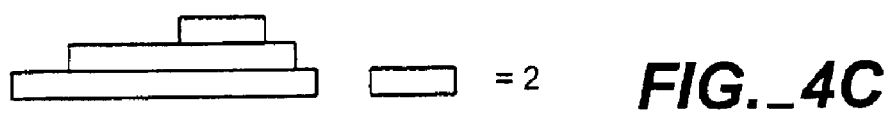
FIG._4C
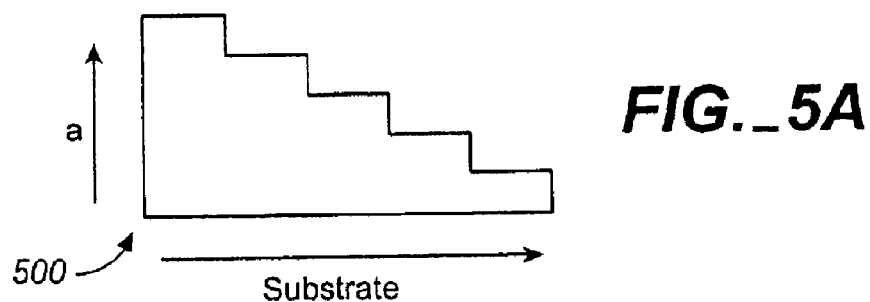
FIG._5A
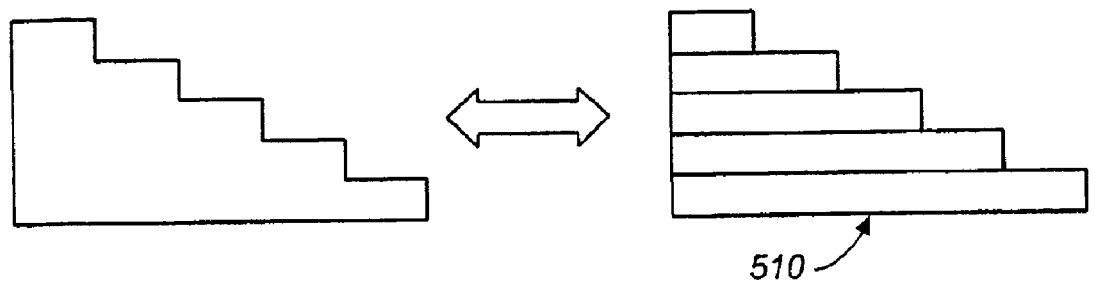
FIG._5B

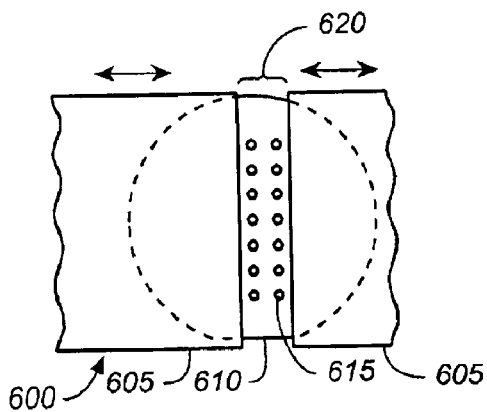
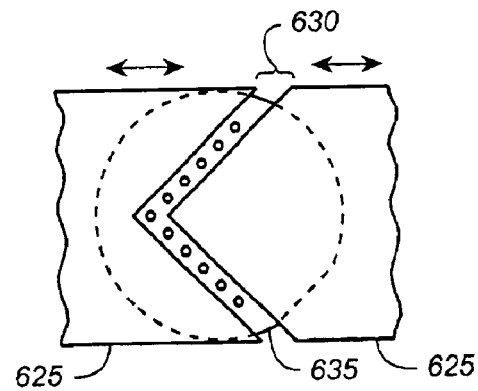
FIG._6A    FIG._6B
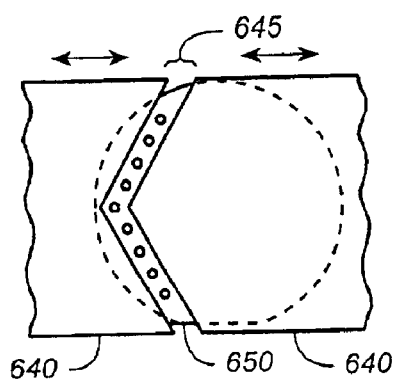
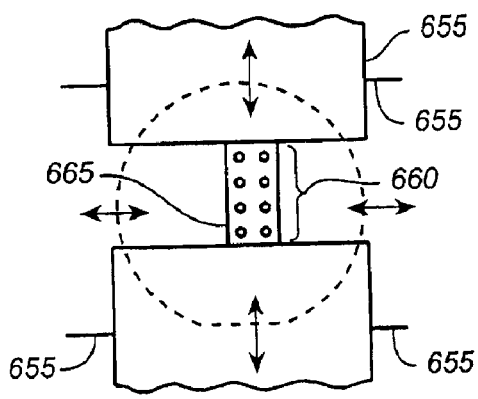
FIG._6C    FIG._6D
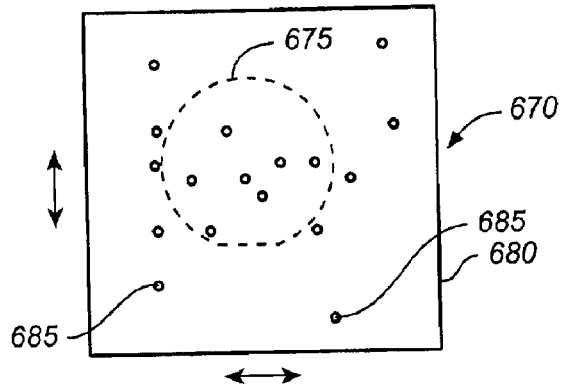
FIG._6E

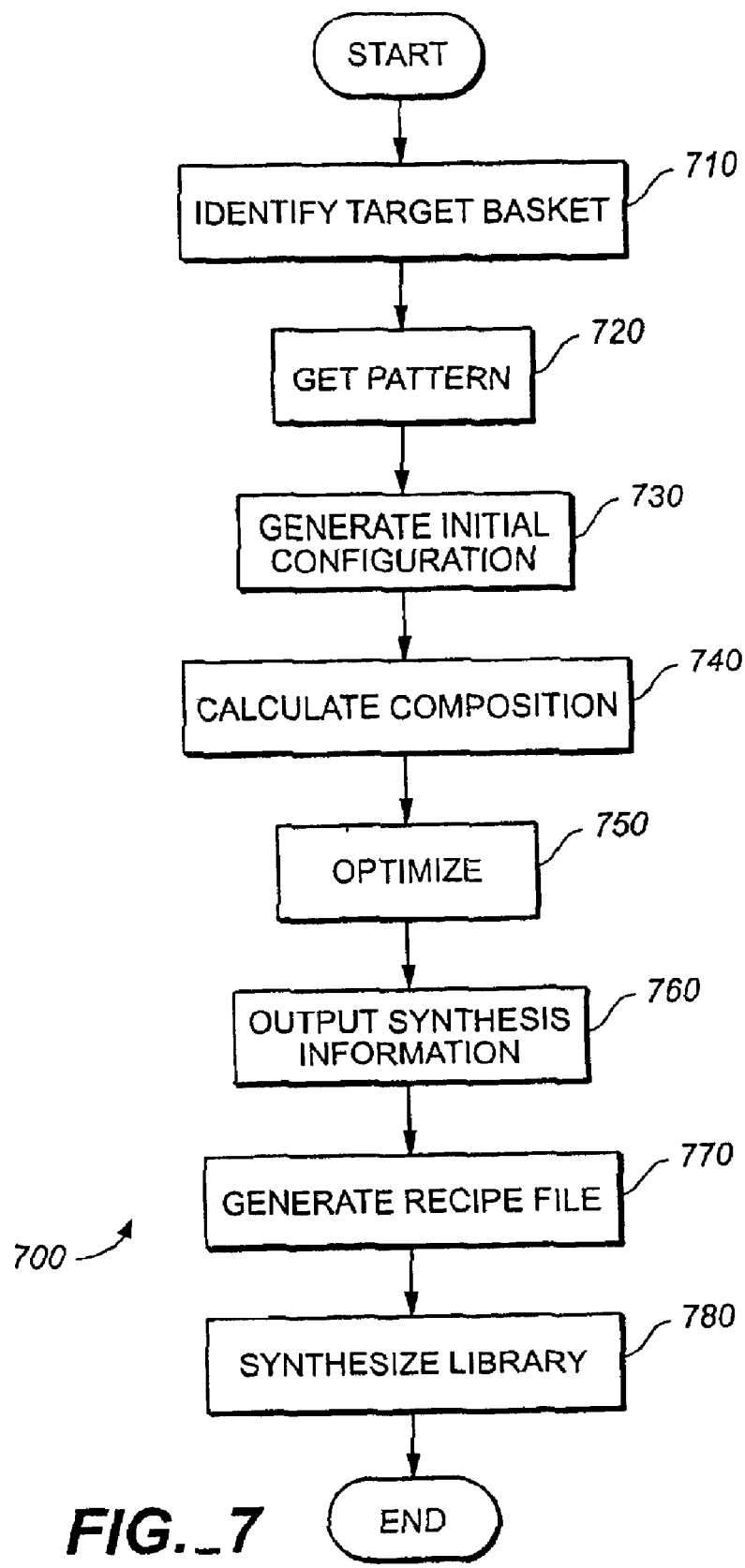
FIG._7

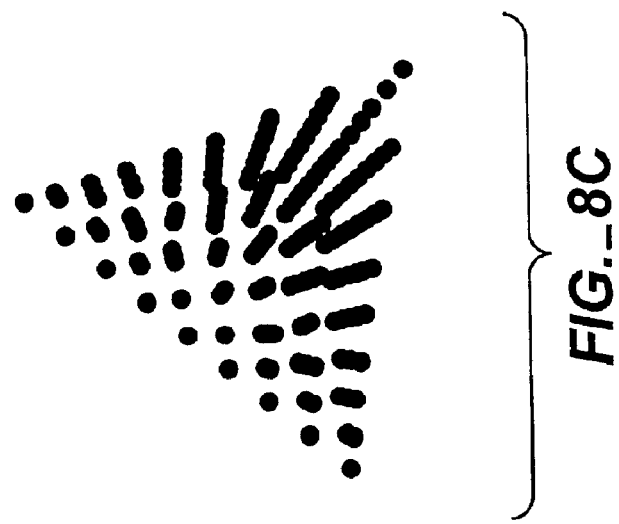
*FIG._8C*
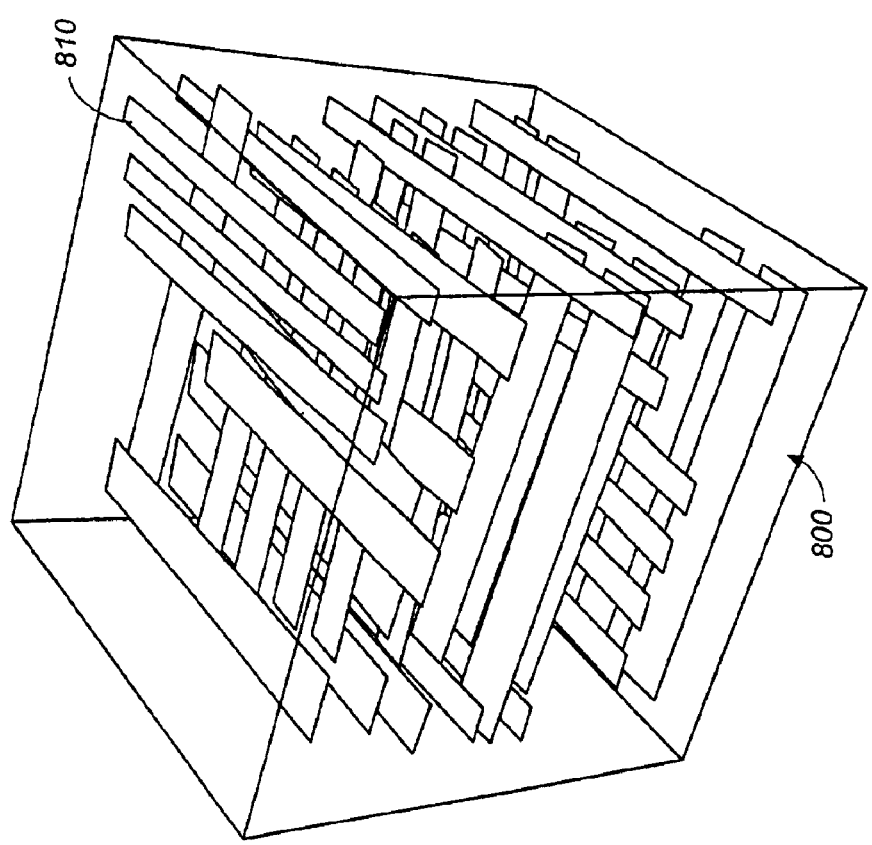
*FIG._8A*

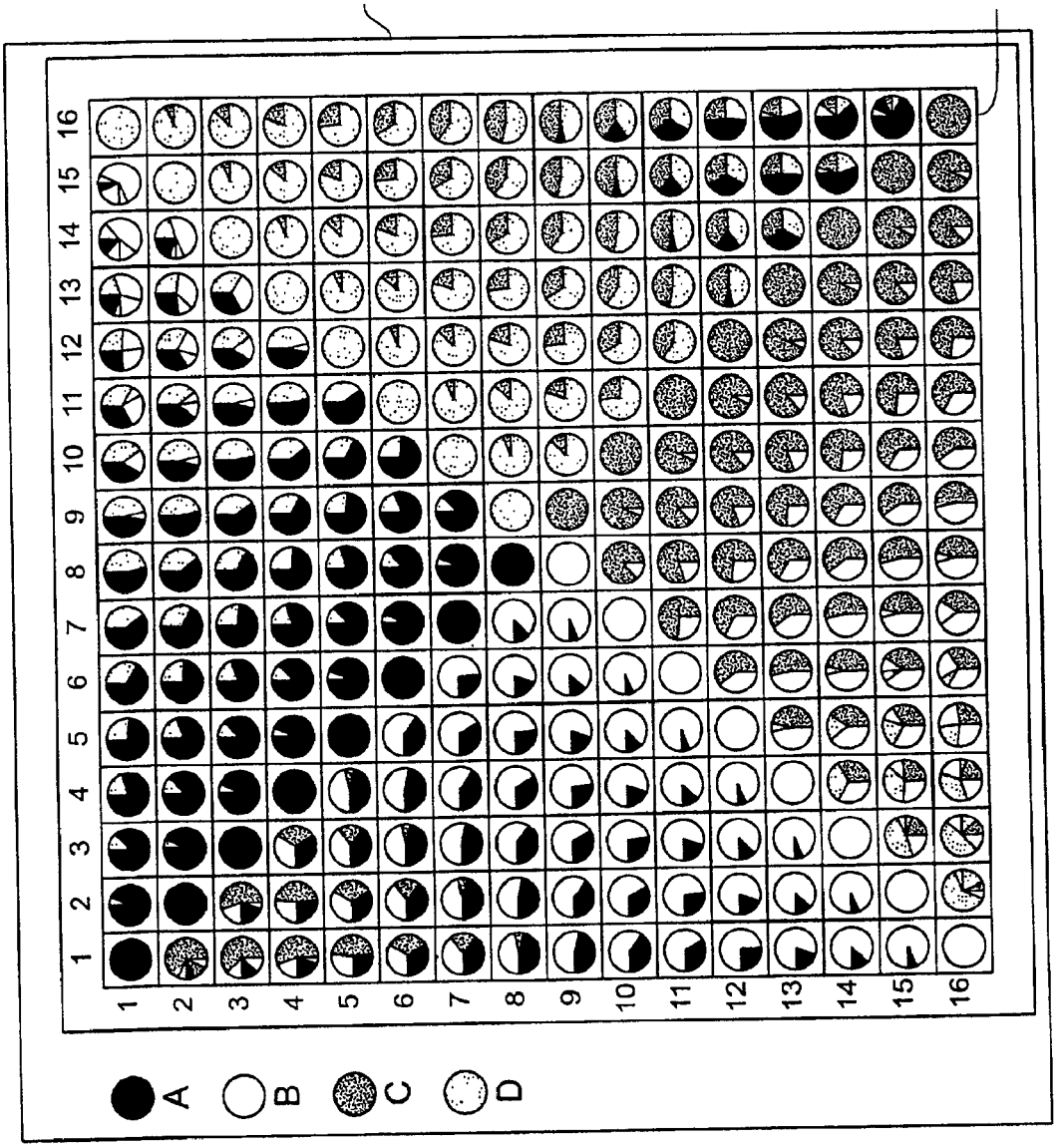
FIG._8B

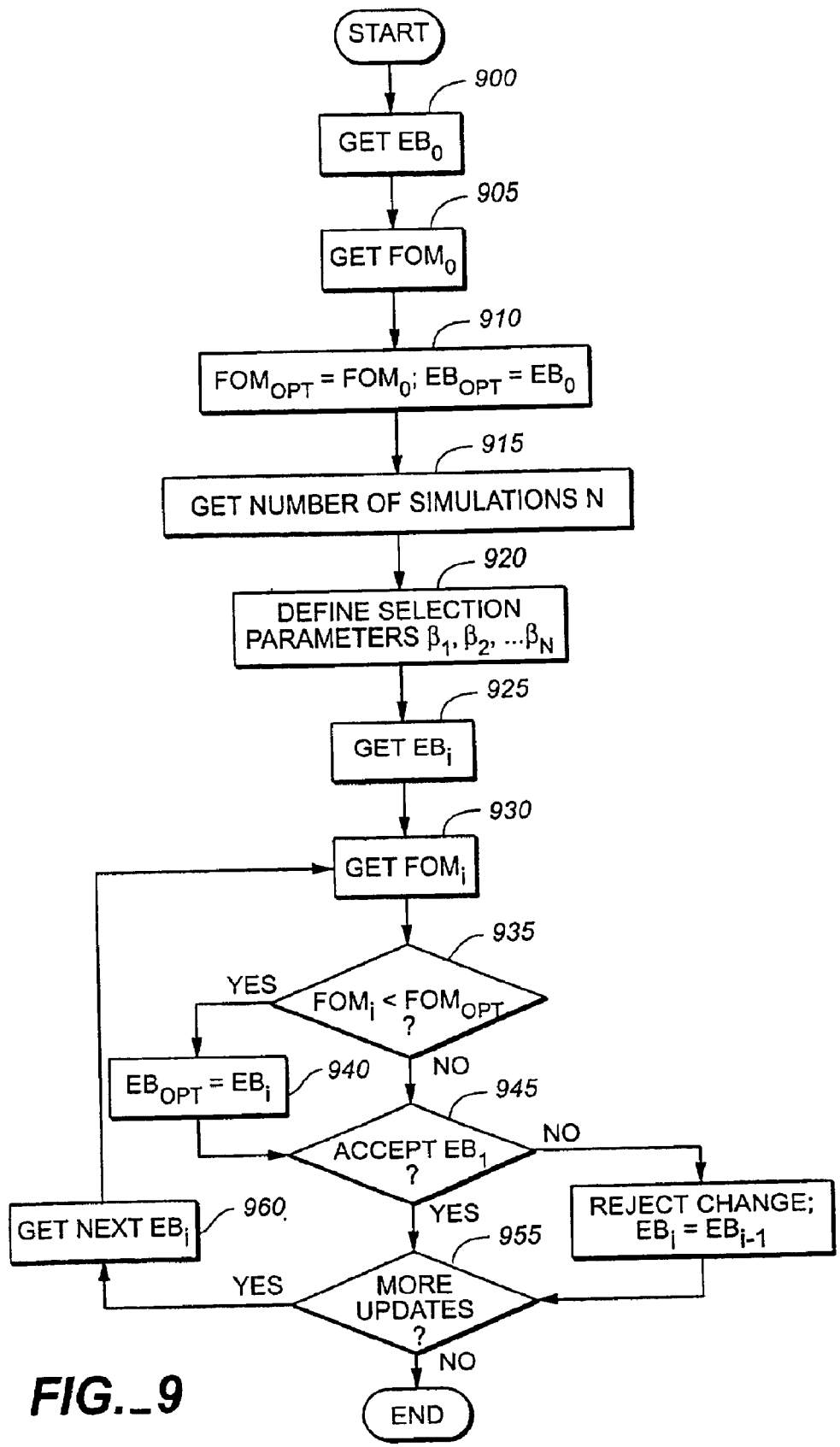
FIG._9

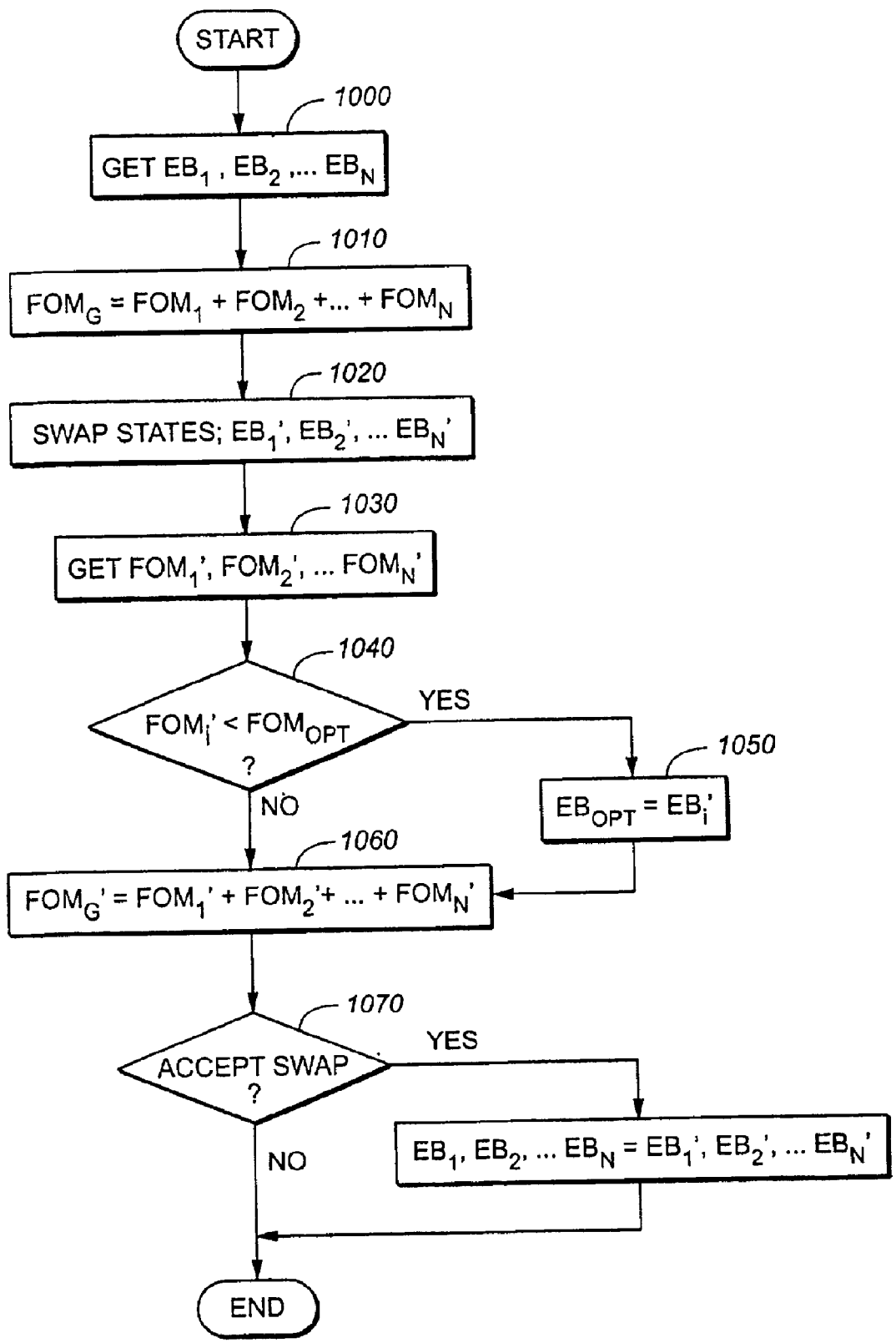
FIG._10

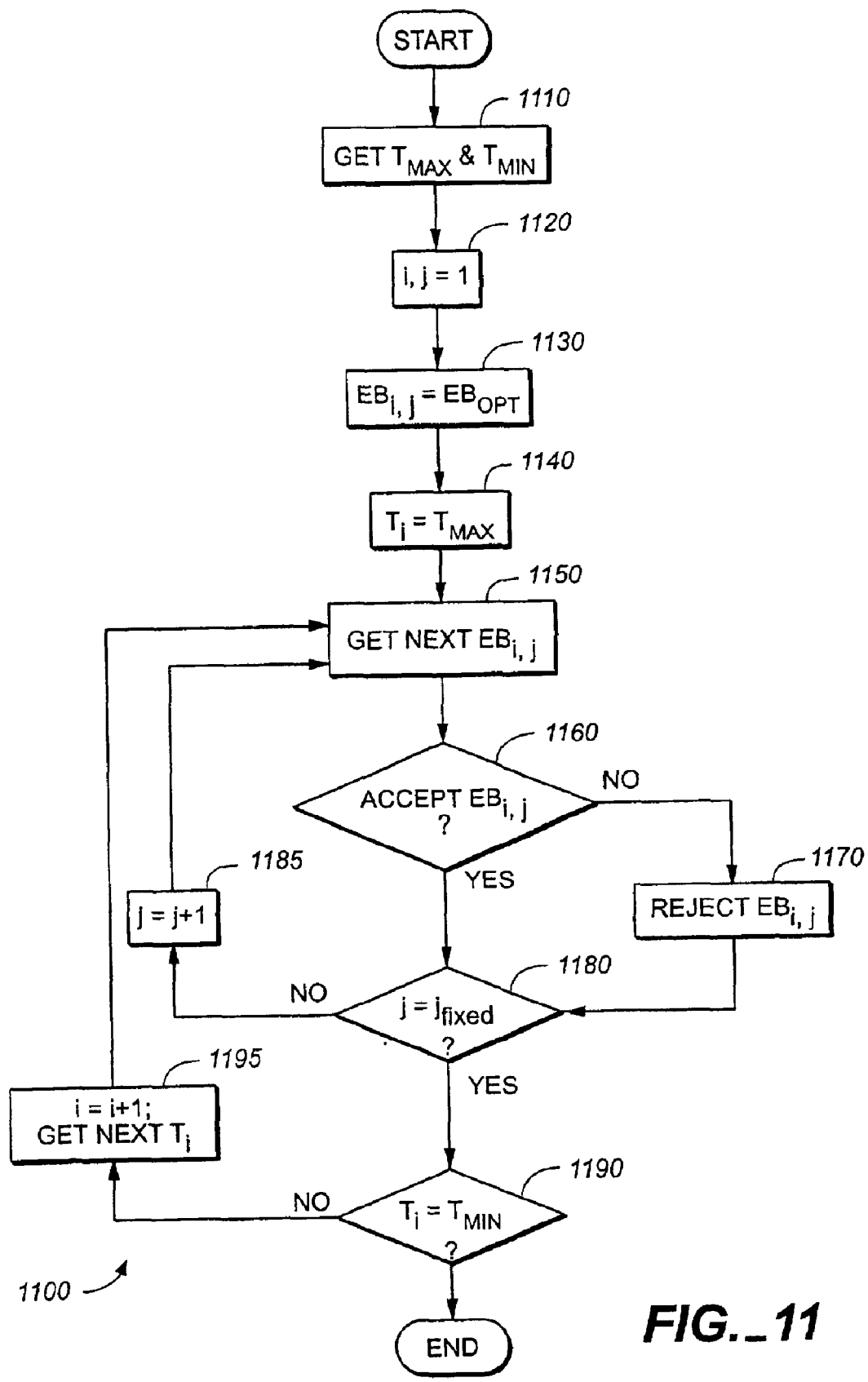
FIG._11

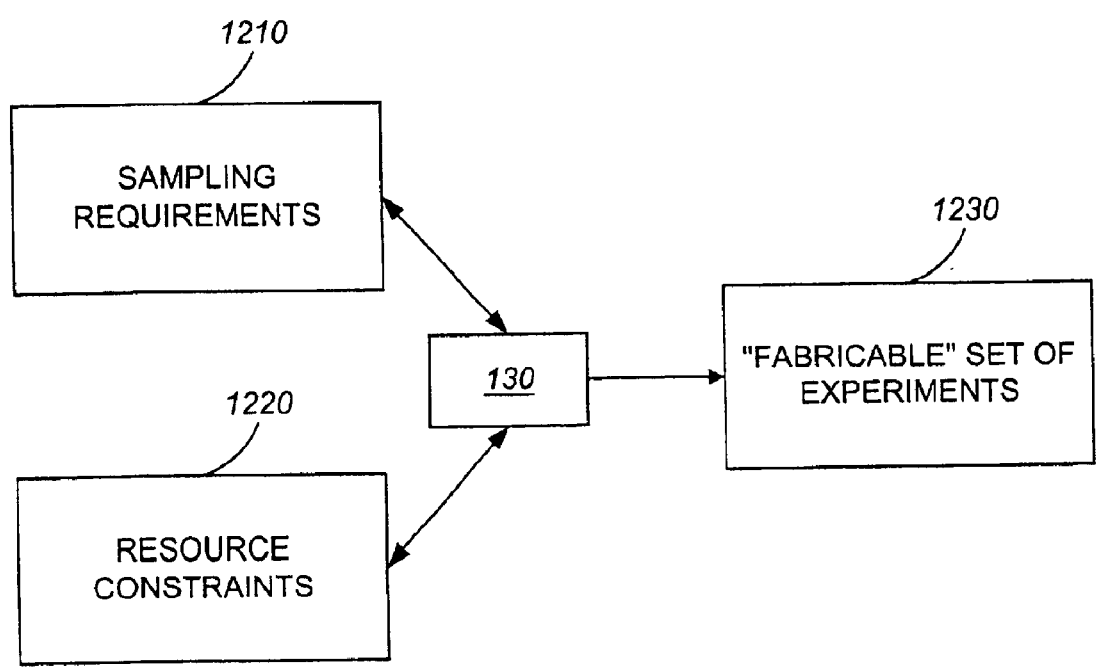
FIG._12

METHODS AND APPARATUS FOR PREPARING HIGH-DIMENSIONAL COMBINATORIAL EXPERIMENTS

CROSS-REFERENCE TO RELATED APPLICATIONS

This application claims the benefit of Provisional Application No. 60/256,270, filed on Dec. 15, 2000, which is incorporated by reference herein.

STATEMENT REGARDING FEDERALLY SPONSORED RESEARCH

The U.S. Government has a paid-up license in this invention and the right in limited circumstances to require the patent owner to license others on reasonable terms as provided for by the terms of contract No. N00014-98-C-0288 awarded by the Office of Naval Research.

TECHNICAL FIELD

This invention relates to methods and apparatus for designing and preparing experiments.

BACKGROUND

There is currently a tremendous amount of activity directed toward the discovery and optimization of materials and material systems such as phosphors, polymers, pharmacological compounds, semiconducting solids, and devices and the like. These new materials are typically useful because they have superior values for one or several properties. These properties could include (but are not limited to) electrical conductivity, color, bio-inertness, fabrication cost, or any other property. A variety of fields (pharmacology, chemistry, materials science) focus on the development of new materials and devices with superior properties. Unfortunately, even though the chemistry of both small molecules and extended solids has been extensively explored, few general principles have emerged that allow one to predict with certainty the composition, structure, and reaction pathways for synthesis of such materials. New materials are typically discovered through experimentation, rather than designed from existing principles.

The ability to discover new materials presupposes (1) the ability to actually make the material, and (2) the ability to accurately measure the properties of interest, or other properties that correlate with the properties of interest. Development of a material with superior properties also requires (3) the ability to make materials that are different in some way—meaning that the materials are in some sense not identical, whether in composition, molecular structure, processing history, raw material source, or any other difference that might impact a material's properties—and (4) a way to compare the properties of the different materials.

A common challenge is understanding how two materials actually differ from each other. Any two materials might be similar in one or many ways (e.g., composition) but different in many other ways. Thus, the properties of one material might be "better" (for a particular purpose) than those of another material for any number of reasons. One goal of experimental science is determining how properties vary with different parameters. In this sense, a parameter is any variable whose value can change in either a continuous or discontinuous fashion. Parameters can include concentrations of different chemical species (e.g., elements, compounds, solvents), temperature, annealing time, molecular weight, exposure time to radiation, process sequence or any other variable. Experimental studies typically examine the variation of a given property (e.g., smell) with a measured parameter (e.g., molecular weight), often with the implicit assumption that all other parameters are held constant (i.e., their values are identical for the compared samples). In the ideal case, two materials only differ in one parameter, and variation in the measured property is construed to be caused by variation in this parameter.

Unfortunately, it is difficult or impossible to completely determine how two materials are "different". While variation in a given parameter (e.g., chemical composition) might be fairly obvious (e.g., one sample has 20% more nitrogen than the other), variation in another parameter might remain hidden (e.g., one sample has a slightly preferred grain orientation, vs. another sample's random orientation). The challenge is determining which parameters have a significant effect on the property of interest. This challenge requires the examination of the effects of many different parameters on the desired properties. Variation in each of these parameters creates a parameter space: a high-dimensional space defined by all the relevant parameters that describe a material. A single material is thus defined by its coordinates within this parameter space—the values for each of these parameters for the given material. The goal of materials development is finding the coordinates of the material with the best set of desired properties. The commonly used analogy "looking for a needle in a haystack" can loosely describe this process: the parameter space is the "haystack", and the material(s) with the best set of properties is (are) the needle(s).

Traditionally, the discovery and development of various materials has predominantly been a trial and error process carried out by scientists who generate data one experiment at a time—in other words, each axis in the parameter space is examined serially. This process suffers from low success rates, long time lines, and high costs, particularly as the desired materials increase in complexity. Nevertheless, these methods have been successful for developing materials whose properties are governed by a relatively small number of parameters.

However, many properties can be a function of a large number of different parameters. Additionally, the combined effects of parameter variation can be much more complicated than the discrete effects of varying one or two parameters by themselves. For such a property, a very large parameter space must be examined in order to find the material with the best properties. As a result, the discovery of new materials often depends largely on the ability to synthesize and analyze large numbers of new materials over a very broad parameter space. For example, one commentator has noted that to search the system of organic compounds of up to thirty atoms drawn from just five elements—C, O, N, S and H—would require preparing a library of roughly $10^{63}$ samples (an amount that, at just 1 mg each, is estimated to require a total mass of approximately $10^{60}$ grams—roughly the mass of $10^{27}$ suns). See W. F. Maier, "Combinatorial Chemistry—Challenge and Chance for the Development of New Catalysts and Materials," Angew. Chem. Int. Ed., 1999, 38, 1216. When material characteristics vary as a function of process conditions as well as composition, the search becomes correspondingly more complex. One approach to the preparation and analysis of such large numbers of compounds has been the application of combinatorial methods.

In general, combinatories refers to the process of creating vast numbers of discrete, diverse samples by varying a set of parameters in all possible combinations. Since its introduction into the bio- and pharmaceutical industries in the late 80's, it has dramatically sped up the drug discovery process and is now becoming a standard practice in those industries. See, e.g., Chem. Eng. News, Feb. 12, 1996. Only recently have combinatorial techniques been successfully applied to the preparation of materials outside of these fields. See, e.g., E. Danielson et al., SCIENCE 279, pp. 837–839, 1998; E. Danielson et al., NATURE 389, pp. 944–948, 1997; G. Briceno et al., SCIENCE 270, pp. 273–275, 1995; X. D. Xiang et al., SCIENCE 268, 1738–1740, 1995. By using various rapid deposition techniques, array-addressing strategies, and processing conditions, it is now possible to generate hundreds to thousands of diverse materials on a substrate of only a few square inches. These materials include, e.g., high Tc superconductors, magnetoresistors, and phosphors. Using these techniques, it is now possible to create large libraries of chemically diverse compounds or materials, including biomaterials, organics, inorganics, intermetallics, metal alloys, and ceramics, using a variety of sputtering, ablation, evaporation, and liquid dispensing systems as disclosed, for example, in U.S. Pat. Nos. 5,959,297, 6,004,617, 6,030,917 and 6,045,671, and U.S. application Ser. No. 09/119,187, filed on Jul. 20, 1998, each of which is incorporated by reference herein.

An implicit goal of any experimental study is getting the most information for the minimum cost (including time); this goal is especially stringent for large parameter spaces that require vast numbers of experiments. This requires (1) maximizing the information content of each experimental point, and (2) minimizing the resource cost to synthesize and measure each experimental point. The process of deciding where in the parameter space to make and measure samples is called "sampling" or "populating" the parameter space. This process requires choosing a plurality of points in the space representing materials for synthesis and measurement. A subsequent, equally important requirement is actually making and measuring samples with the desired coordinates.

As discussed previously, the parameter spaces to which combinatorial methods are typically applied are often very large. Additionally, small changes in the values of parameters can have a large change on properties. As a result, the effective design and preparation of combinatorial libraries is a crucial factor in the success of a combinatorial project. This requirement (the process of choosing points for experimentation that have the most information at lowest cost) is described herein as efficient sampling of the parameter space. The goal of efficient sampling is choosing the minimum number of points for evaluation (synthesis and measurement) while still achieving a material with the desired set of properties. While efficient sampling is of course important for low dimensional parameter spaces, it is critical for cost effective exploration of high dimensional parameter spaces.

Regardless of the dimensionality of the relevant parameter space, historical experimentation has almost always been based upon synthesis and measurement of lower dimensional spaces (e.g., slices or projections). The ease with which humans interpret graphical data has led to the design of most experiments as evaluation of the response of a single dependent variable (y) on a single independent variable (x). Indeed, scientists using combinatorial methods have often designed combinatorial libraries by transposing a two dimensional projection from the parameter space onto a (two-dimensional) plane. For a given N-dimensional parameter space, N-2 parameters are constrained by the scientist, such that only 2 parameters vary independently across the library. This variation may be achieved by creating a set of gradients that define composition change across the library, or by defining a set of linear equations for distributing components to various locations on the substrate, or other ways.

Because the dimensionality of the projection is the same as the dimensionality of the substrate (i.e., a dimensionality of two), it is often easy to correlate the variation of points across the library with variation across the parameter space, which can aid interpretation. Additionally, it might often be relatively easier to perform the physical synthesis process (i.e., make the library) when the parameter space is sampled using projections. As a result, many combinatorial libraries are made by directly transposing different two-dimensional projections onto a two-dimensional substrate or other carrier. This method is useful for a large range of unexplored materials (e.g., ternary composition diagrams), so has found extensive use for low-dimensional parameter space explorations.

However, direct transposition of projections, whether by gradients, equations, or other methods, may not be the most efficient way to sample high-dimensional parameter spaces. Indeed, the ease with which 2-D projections can be designed, synthesized, and interpreted has often taken precedence over higher-dimensional sampling strategies that could be more efficient. Additionally, inferring the variation of properties in high-dimensional spaces using only data from multiple projections through the space can lead to erroneous conclusions for complex systems.

In summary, the sampling strategy for the vast majority of prior scientific work is a result of either human interpretive limitations (for example, not being able to "see" in high dimensions) or equipment limitations. More precisely, for many combinatorial studies, the library design process has yielded the sampling strategy, not the other way around. While this is sufficient if a given library design yields an efficient sampling, it is not optimal if the library design does not yield an efficient sampling.

SUMMARY

The invention provides methods and apparatus for efficiently designing and performing experiments. In general, in one aspect, the invention provides computer-implemented methods and apparatus, including computer program apparatus, implementing techniques for designing a set of experiments to be performed with a set of resources. The techniques include providing a set of parameters and a set of constraints including one or more experimental constraints representing limitations on operations that can be performed with the set of resources, generating a plurality of configurations based on the parameters and the experimental constraints, selecting a configuration from the plurality of configurations, and defining a set of experiments based on the selected configuration. The parameters include a plurality of factors to be varied in a set of experiments and represent axes defining a parameter space. Each configuration includes a plurality of experimental points. Each point has a set of values for the parameters Particular implementations can include one or more of the following features. The set of constraints can include one or more experiment lattices or lattice points, representing an arrangement in which experiments in a set of experiments will be performed. The lattice points can represent locations on a substrate. The set of constraints can include a set of one or more patterns representing the application of parameters to one or more lattice points of an experiment lattice under a set of experimental constraints represented by a set of attributes. Generating a plurality of configurations can include generating a plurality of instances of one or more of the patterns, each pattern instance being defined by a set of attribute values specifying a quantity of a parameter to be applied at one or more lattice points of an experiment lattice, and combining the pattern instances to generate a configuration, such that the parameter values for a point in the configuration are based on the parameter values specified by the combined pattern instances for a corresponding lattice location.

The patterns can include one or more device patterns having attributes representing constraints associated with one or more devices for performing operations at one or more locations represented by lattice points of the experiment lattice. The operations can include process steps for applying parameters at the locations. The process steps can include depositing materials at one or more locations. The process steps can include subjecting materials at one or more locations to processing conditions. The device pattern attributes for one or more device patterns can include one or more device geometry attributes specifying a geometry in which a parameter will be applied to a substrate. The device geometry attributes can include a thickness attribute representing a quantity of the parameter to be applied. The device patterns can represent openings in a mask for exposing locations on a substrate. The device patterns can represent openings in a shutter mask system for exposing locations on a substrate. The device patterns can represent a set of dispensing tips for delivering materials to locations on a substrate. The plurality of pattern instances can include a plurality of device pattern instances specifying amounts of one or more materials to be deposited at locations on a substrate.

The set of constraints can includes one or more component patterns representing an arrangement of materials to be used in performing a set of experiments. Generating a plurality of pattern instances can include superimposing the pattern instances with the component patterns, such that the pattern instances represent the application of the arrangement of materials to lattice points of the experiment lattice. The component patterns can include a component pattern representing a library lattice for a parent library of materials to be used in performing a set of experiments.

Combining the pattern instances can include superimposing a plurality of pattern instances with one or more experiment lattices. The configurations can represent sets of experiments that can be performed with the set of resources. The plurality of configurations can be generated by repeatedly generating and combining pattern instances. Generating a plurality of configurations can include generating a plurality of sets of pattern instances by varying the number and/or attribute values of pattern instances. Generating a plurality of configurations can include generating a first configuration and subsequently generating a sequence of second configurations, each of the second configurations being generated by adding a pattern instance to a preceding configuration in the sequence, removing a pattern instance from a preceding configuration in the sequence, or changing an attribute value for an attribute of a pattern instance in a preceding configuration in the sequence. The first configuration can be a pseudo-random configuration.

Selecting a configuration from the plurality of configurations can include calculating a figure of merit for each of the configurations and applying a selection rule to the calculated figures of merit. The figure of merit can be calculated by comparing parameter space points for an experimental configuration with a set of sampling requirements for a desired set of experiments. The set of sampling requirements can include a set of target points representing a desired set of experiments. The selected configuration can be required to include a point corresponding to each point in the set of target points. The figure of merit can be calculated as a function of a distance in the parameter space between points in the configuration and points in the set of target points. The figure of merit can be calculated as a function of the resource cost to perform a set of experiments defined by the experimental points in the configuration. The resource cost for a configuration can be determined as a function of the number of patterns from which the configuration was generated.

Generating a plurality of configurations and selecting a configuration can include performing an optimization process. The optimization process can be selected from Monte Carlo processes, simplex processes, conjugate gradient processes, genetic algorithm processes and other processes. The optimization process can include a Monte Carlo optimization process based on simulated annealing, parallel tempering, or a combination thereof.

Combining the pattern instances can include defining a sequence of pattern instances, such that the points in the configuration are defined in part by order information derived from the sequence. Generating a plurality of configurations can include generating a first configuration and subsequently generating a sequence of second configurations, with each second configuration being generated by adding a pattern instance to a preceding configuration in the sequence, removing a pattern instance from a preceding configuration in the sequence, changing an attribute value for an attribute of a pattern instance in a preceding configuration in the sequence, or changing the position of a pattern instance in the sequence. Selecting a configuration can include identifying an optimum sequence of events for the set of experiments.

The set of patterns can include patterns representing alternate applications of parameters to lattice points of an experiment lattice. The set of patterns can include a first pattern defined by a first set of attributes and a second pattern defined by a second set of attributes, with the second set of attributes differing from the first set of attributes in at least one attribute. Generating a plurality of configurations can include combining instances of the first pattern to generate a first configuration and combining instances of the second pattern to generate a second configuration. Selecting a configuration can include identifying an optimum pattern from the first and second patterns.

The experiment lattices can include a first experiment lattice representing a first arrangement in which a set of experiments could be performed and a second experiment lattice representing a second arrangement in which the set of experiments could be performed. Generating a plurality of configurations can include superimposing pattern instances with the first experiment lattice to generate a first configuration and superimposing pattern instances with the second experiment lattice to generate a second configuration. Selecting a configuration can include identifying an optimum experiment lattice from the first and second experiment lattices.

The component patterns can include a first component pattern representing a first arrangement of materials that could be used in performing the set of experiments and a second arrangement of materials that could be used in performing the set of experiments. Generating a plurality of configurations can include generating a first configuration based on the first component pattern and a second configuration based on the second component pattern. Selecting a configuration can include identifying an optimum component pattern from the first and second component patterns.

Defining the set of experiments based on the selected configuration can include introducing a change to the selected configuration and defining the set of experiments based on the changed configuration. The set of constraints can include a first set of experimental constraints representing limitations on operations that can be performed with a first set of resources and a second set of experimental constraints representing limitations on operations that can be performed with a second set of resources. Generating a plurality of configurations can include generating a first configuration based on the first set of experimental constraints and a second configuration based on the second set of experimental constraints. Selecting a configuration can include identifying an optimum set of resources from the first and second sets of resources. The techniques can include outputting electronic data representing a design for the set of experiments.

In general, in another aspect, the invention provides computer-implemented methods and apparatus, including computer program apparatus, implementing techniques for designing a set of experiments to be performed with a set of resources. The techniques include providing a set of parameters, one or more experiment lattices, and one or more patterns, generating a plurality of instances of one or more of the patterns, combining the pattern instances to generate a set of experimental points, defining a set of experiments based on the experimental points. The parameters include a plurality of factors to be varied in a set of experiments and represent axes defining a parameter space. Each experiment lattice includes one or more lattice points and represents an arrangement in which experiments in a set of experiments will be performed. Each pattern representing the application of a parameter to one or more lattice points of an experiment lattice under a set of experimental constraints representing limitations on operations that can be performed with the set of resources. The experimental constraints for a given pattern are represented by a set of attributes. Each pattern instance is defined by a set of attribute values for the attributes defining the pattern. The set of attribute values for a pattern specifies a quantity of a parameter to be applied at one or more lattice points of an experiment lattice. Each point has a set of values for the parameters based on the parameter values specified by the combined pattern instances for a corresponding lattice location.

In general, in another aspect, the invention provides systems for performing a set of experiments. The systems include one or more devices configured to apply a plurality of parameters to a plurality of locations on a substrate and a programmable processor. The parameters include a plurality of factors to be varied in a set of experiments and represent axes defining a parameter space. The application of parameters to the substrate locations is defined by one or more patterns. Each pattern represents the application of a parameter to one or more substrate locations under a set of experimental constraints representing limitations on operations that can be performed with the devices. The experimental constraints for a given pattern are represented by a set of attributes. The programmable processor is configured to generate a plurality of instances of one or more of the patterns, combine the pattern instances to generate a configuration, define a design for a set of experiments based on the configuration, and instruct the devices to carry out the set of experiments according to the design. Each pattern instance is defined by a set of attribute values for the attributes specifying a quantity of the parameter to be applied at one or more locations on the substrate. Each configuration includes a plurality of experimental points. Each point has a set of values for the parameters based on the quantities specified by the combined pattern instances for a corresponding substrate location. The design includes for each experiment in the set of experiments a set of parameter values quantifying each of a plurality of the parameters to be applied in the experiment.

In particular implementations, the programmable processor can be configured to provide a set of target points representing a desired set of experiments, generate a plurality of configurations, select an configuration from the plurality of experimental configurations based on a comparison of the points in the configurations to the set of target points, and define the design for the set of experiments based on the selected configuration. The set of target points can include a plurality of points in a parameter space defined by a plurality of experimental parameters. Each of the points in the set of target points can have a set of parameter values. The plurality of configurations are generated by generating a plurality of sets of pattern instances and combining the instances of each set of the pattern instances. Each configuration includes a plurality of points in the parameter space.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a block diagram illustrating a system for designing a set of experiments.

FIGS. 2A–B illustrate experiment lattices suitable for synthesizing a library of materials.

FIGS. 3A–C illustrate a physical vapor deposition tool for synthesizing a library of materials.

FIG. 4 illustrates deposition profiles for a series of components during synthesis of a library of materials.

FIGS. 5A–B illustrate deposition profiles of a component during synthesis of a library of materials.

FIGS. 6A–E illustrate a series of masking systems for synthesizing a library of materials.

FIG. 7 is a flow diagram illustrating a method of synthesizing a high-order library of materials on a two-dimensional substrate.

FIG. 8A is a graphical representation of a configuration of patterns representing a high-dimensional library design.

FIGS. 8B–C illustrate composition maps for the library design of FIG. 8A.

FIG. 9 is a flow diagram illustrating portions of a parallel tempering optimization method.

FIG. 10 is a flow diagram further illustrating a parallel tempering optimization method.

FIG. 11 is a flow diagram illustrating a simulated annealing optimization method.

FIG. 12 is a flow diagram illustrating multiple modes of operation of a library optimization system.

Like reference symbols in the various drawings indicate like elements.

DETAILED DESCRIPTION

FIG. 1 illustrates a system 100 for designing and preparing a set of experiments. System 100 includes one or more experimental devices 140, such as a physical vapor deposition tool, a liquid dispensing robot or other appropriate device, as discussed in more detail below. System 100 also includes a general-purpose programmable digital computer system 110 of conventional construction, including a memory 120 and a processor for running a library optimization program 130. Computer system 110 is coupled to device 140. Users interact with system 100 through input/output devices 150. Although FIG. 1 illustrates design system 100 as being implemented on a single computer system, the functions of system 100 can be distributed across multiple computer systems, such as on a network.

As used in this specification, a library of materials is a matrix having two or more members, generally containing some variance in chemical or material composition, amount, structures, reaction conditions, and/or processing conditions (including order of process), where a member represents a single library constituent, location, or position containing one set of chemicals or materials subject to one set of reaction or processing conditions. Libraries can include physical arrays of materials, with different materials located at different regions of a substrate. Libraries can also include physical arrays of otherwise similar materials, with different regions of the substrate subject to different process conditions or process order or any other physical application that creates diversity. The concept of "library" can also be extended to a plurality of substrates. In this sense, a library can be defined as any matrix of sites, having two or more members, with parametric diversity between members (or lack thereof, e.g. for error analysis and control purposes), arranged in such a way that physical processes (e.g., synthesis, characterization, or measurement) can be implemented. In one implementation, each library includes one or more members, each of which may be represented as a region in an arrangement (e.g., an array) of one or more regions. A library can include any number of members—for example, two or, more preferably, four, ten, twenty, hundreds or even thousands or more members. Library members are three dimensional regions of the library that can be thought of as single points in parameter space. In this specification, library members may also sometimes be referred to as points or sites.

Libraries are typically prepared on a physical carrier or substrate, and the members of a library may, but need not necessarily, correspond to locations on or in the substrate (such as a microtiter plate, wafer, gel, foam or the like) on which the library was or will be created. Essentially, any conceivable substrate can be employed in the invention. The substrate can be organic, inorganic, biological, nonbiological, or a combination of any of these, existing as particles, strands, precipitates, gels, sheets, tubing, spheres, containers, capillaries, pads, slices, films, plates, slides, foams, etc. The substrate can have any convenient shape, such a disc, square, sphere, circle, etc. The substrate is often flat, but may take on a variety of alternative surface configurations. For example, the substrate may contain raised or depressed regions on which the synthesis of diverse materials takes place. The substrate may form a rigid or flexible support on which to carry out the processes described herein.

The substrate may be any of a wide variety of materials including, for example, polymers, plastics, resins, silicon, silica or silica-based materials, carbon, metals, inorganic glasses, inorganic crystals, membranes, etc. Other substrate materials will be readily apparent to those of skill in the art upon review of this disclosure. Surfaces on the solid substrate can be composed of the same materials as the substrate or, alternatively, they can be different, i.e., the substrates can be coated with a different material. Moreover, the substrate surface can contain thereon an adsorbent (for example, cellulose) to which the components of interest are delivered. The most appropriate substrate and substrate-surface materials will depend on the class of materials to be synthesized and the selection in any given case will be readily apparent to those of skill in the art.

While the library may correspond to the geometry of the ultimate physical substrate, it may also represent a collection of library members on a more conceptual level. Libraries can be represented and/or prepared in any convenient shape, such as square, rectangle, circle, triangle or the like, and in zero dimensions (e.g., a point), one dimension (e.g., a linear array of points on a wire), two dimensions (e.g., a surface or plate), or three dimensions (e.g., a block of gel, or other volumetric carrier), depending, for example, on the underlying chemistry or apparatus involved. In mathematical terms, a region on a substrate can be abstracted as a point. Therefore a zero-dimensional carrier substrate includes a single point, a one-dimensional carrier includes one or more than one point, etc. In general, a substrate can be viewed as carrying a set of points.

In one class of substrates, the spatial relationships between the points are or can be predefined and retained during library preparation—in other words, the substrate is spatially addressable. In such substrates, the spatial relationship among the points on the substrate can be used to identify, recognize, or address regions, particularly regions of interest.

A set of points having predefinable and retainable spatial relationship is described herein as a "lattice". Thus, a series of points on a wire is an example of one-dimensional lattice, while a plate having 7 rows of 7 wells each is a two-dimensional (square) lattice with a 7 by 7 arrangement, as illustrated in FIG. 2A. FIG. 2B illustrates another example of a two-dimensional lattice—a honeycomb of hexagons in which each vertex defines a lattice point. The set of points at which a set of experiments is to be performed will be called an "experiment lattice".

In the context of materials science, a material can be described as a combination of one or more ingredients or components. The implicit advantage of combinatorial methods is that many diverse materials can be rapidly synthesized and analyzed for one or more desirable characteristics, referred to in this specification as "properties". A property is a quantifiable characteristic of a material, which can include, for example, electrical properties, thermal properties, mechanical properties, morphological properties, optical properties, magnetic properties, chemical properties, and the like. A property can result from the presence of a single discrete material, or a combination of discrete materials, or a combination of discrete materials in a particular arrangement or order, or any other combination. More particularly, properties that can be screened for include, for example, super-conductivity, resistivity, therapeutic efficacity against a physiological condition, thermal conductivity, anisotropy, hardness, crystallinity, optical transparency, magnetoresistance, permeability, frequency doubling, photoemission, coercivity, dielectric strength, or other useful properties which will be apparent to those of skill in the art upon review of this disclosure. Because each material must be fabricated before it can be analyzed, rapid synthesis of diverse materials is an initial requirement of any combinatorial study. In general, a material's properties can be measured experimentally and are a function of other, known or unknown, characteristics of the material, which, in this specification, will be referred to as "parameters".

A parameter is a quantifiable variable, whose variation can lead to a change in a given property. According to this definition, parameters can include, for example, process parameters such as temperature, pressure, pH, and exposure time, as well as physical parameters such as composition, molecular weight, and grain size. While there can be overlap between properties and parameters, for the purposes of this specification, it is assumed that parameters can be controlled as inputs in the experimental process, whereas properties are what results. The set of parameters that define a particular material can be thought of as dimensions in a multidimensional parameter space—a mathematical construct composed of composition space and process parameter space—with a given set of parameter values defining a unique point in the parameter space corresponding to a set of composition and processing parameters.

In this specification, the symbol $\Delta_\mu$, is used to represent a discrete parameter space approximating a portion of the general parameter space by uniform sampling of that portion of the space. The creation of an approximate parameter space $\Delta_\mu$ is described in more detail in U.S. Provisional Application No. 60/198,208, filed Apr. 19, 2000, which is incorporated by reference herein in its entirety.

For the sake of clarity, the following discussion is limited to materials defined by a set of components defining a composition space; one skilled in the art will recognize that the principles discussed are equally applicable to experiments defined in a broader parameter space incorporating process parameters in addition to chemical composition.

A material can be represented as $A_a B_b C_c D_d \ldots$, where A, B, C, D, ..., represent the set of components defining the composition space, and a, b, c, d; ..., are composition variables representing the fractional amount of the corresponding component. This formula representation emphasizes the material's composition but ignores other characteristics of the material, such as structure. For some classes of materials, such as biomolecules, organic species, polymers and the like, a material represented by the formula $A_a B_b C_c D_d \ldots$ can be different from, e.g., $A_a C_c B_b D_d \ldots$. By contrast, some other classes of materials are invariant under symbolic permutation operations—that is, $A_a B_b C_c D_d \ldots$ and $A_a C_c B_b D_d \ldots$ represent the same material.

For the purposes of this specification, the formula $A_a B_b$ represents only the initial composition of a material. That is, the formula denotes a composition that "starts from" a mixture of a units of component A and b units of component B. The components may or may not react with each other under the conditions to which the composition is subjected. Moreover, even if reaction does occur, there may exist more than one reaction path, which may yield more than one product, and the product may differ from the composition $A_a B_b$. For example, $A_a$ may partially react with $B_b$, or some or all of the components may be vaporized during synthesis and/or processing.

A general composition space is a set containing all $A_a B_b C_c D_d \ldots$, $$\Omega = \{A_a B_b C_c D_d \ldots \}, a, b, c, d, \ldots, \in [0, \infty],$$

(where the second half of the expression indicates that a, b, c, d, etc., are all real numbers that cannot take negative values). In general, a, b, c, d, etc. are continuous variables and independent from each other. Thus, a general composition space is a subspace of Euclidean space. Consequently, the dimension of an unconstrained, general composition space equals the total number of the variables defining the composition space.

It should be noted that the dimensionality of a composition space is defined by the number of independent composition variables. Thus, a study of a class of materials $A_a B_b C_c D_d$, in which one or more than one ingredient is held constant (e.g., d=constant) results in a three-dimensional composition space, since there are only three independent composition variables a, b and c. In such a case, the tag "D" can be dropped from the formulaic representation for sake of clarity, so the constrained composition space is represented as $(A_a, B_b, C_c,)$. It is understood that the composition can include one or more additional components that are held constant in the study.

To avoid searching a potentially huge general composition space, combinatorial materials science techniques may incorporate as much external information as possible in the selection of points for synthesis and evaluation. One way to incorporate a priori knowledge is by establishing one or more additional constraints on the system based on chemical and physical understanding of the composition space at issue. Each constraint added to the system has the effect of reducing the dimensionality (or degrees of freedom) of the composition space, which can therefore be represented as D=N-M, where N is number of components defining $\Omega_f$, and M is the total number of constraints.

One such constraint can be derived from the general observation that, within the context of many inorganic solids, it is generally the case that a material $A_a B_b C_c D_d \ldots$ and a material $A_{2a} B_{2b} C_{2c} D_{2d} \ldots$ are identical. Of course, this is not always the case—most notably, for example, for organic species, where formula representations ignore important structural information, and for some inorganic species such as, e.g., $NO_2$, which is chemically different from $N_2 O_4$. However, where this general observation holds, it follows that the absolute values of the composition variables have no impact on a material's characteristics; instead, materials can be differentiated based on the relative ratios among the composition variables. As a result, the general composition space can be constrained by a requirement that all composition variables should be normalized (i.e., the fractional sum of all components is constrained to equal 100%), such that the composition space can be expressed as $$\Omega = \{A_a B_b C_c D_d \ldots \}, a, b, c, d, \ldots, \in [0,1], a+b+c+d+ \ldots = 1.$$

Depending on the nature of a chemical system in consideration, the existing knowledge about the system, and the purpose of the research, the scientist can further limit the ranges of the composition variables, further reducing the volume of the parameter space to be explored. For example, while the composition variables of a system intended for catalyst research may be allowed to have the full range (e.g., [0, 1]), composition variables for, say, dopants, can be confined to much narrower ranges of values. Thus, a system can generally be represented as $$\Omega = \{A_a B_b C_c D_d \ldots \},$$

$0 \leq a_L \leq a \leq a_H \leq 1, 0 \leq b_L \leq b \leq b_H \leq 1, 0 \leq c_L \leq c \leq c_H \leq 1,$
$0 \leq d_L \leq d \leq d_H \leq 1, \ldots,$ $a+b+c+d+ \ldots = 1.$ where $a_L$, $b_L$, $c_L$, $d_L$, etc., represent lower limits on the composition variables a, b, c, d, etc., and $a_H$, $b_H$, $c_H$, $d_H$, etc., similarly represent upper limits. Likewise, in some cases (e.g., if the electron-counting rule applies), a charge balance constraint can be added to the system. If the composition variables can be categorized into subgroups having further constraints (e.g., if A and B are members of a subgroup together constrained to constitute no more than 50% of the total composition), additional constraints can be added, as discussed generally in U.S. Provisional Application No. 60/198,208, filed Apr. 19, 2000. After all constraints have been defined, the general composition space is reduced to a subspace of interest, represented as $$\Omega_I = \{A_a B_b C_c D_d \ldots\},$$

$$0 \leq a_L \leq a \leq a_H \leq 1,\ 0 \leq b_L \leq b \leq b_H \leq 1,\ 0 \leq c_L \leq c \leq c_H \leq 1,$$

$$0 \leq d_L \leq d \leq d_H \leq 1, \ldots,$$

$$f_1(a, b, c, d, \ldots) \equiv a+b+c+d+\ldots -1=0,$$

$$f_2(a, b, c, d, \ldots) = 0,$$

$$\ldots,$$

$$f_M(a, b, c, d, \ldots) = 0.$$

where each equation $f_i(a, b, c, d, \ldots)=0$ is a constraint expressing in mathematical terms the requirements and conditions imposed on the general composition.

Efficient combinatorial studies often require the sampling of high-dimensional spaces. At one level, the process of designing and preparing a set of experiments using system 100 is one of transforming the dimensionality of different spaces—that is, the transformation of a hypothetical, N-dimensional composition space (or more generally, a high order parameter space as discussed above) to the two-dimensional space of a physical library, where library can be construed as one or more physical substrates or carriers, as described above. In systems having a true dimensionality D that is less than or equal to two, it is a relatively simple matter to map the composition space of interest, $\Omega_I$, onto a two dimensional physical surface, even if N is much larger than 2.

On the other hand, if $D \geq 3$, it can be difficult or impossible to map the corresponding $\Omega_I$ onto a two-dimensional physical surface using traditional schemes. The reason for this difficulty is that higher order spaces (i.e., spaces where $D \geq 3$) contain exponentially more points than spaces of lower dimension (even though lower-dimensional spaces also contain an infinite number of points). Therefore, a simple one-to-one correspondence between the two spaces, a requirement for such mappings, is impossible.

Any continuous space can be approximated by a set of discrete points in that space. In the limit of infinitely many points in the set, where the limit operation is suitably defined, one recovers the original space. As a result, $\Omega_I$ can be approximated by sampling the continuous space in discrete fashion as follows:

$$\Omega_{ID} = \{A_a B_b C_c D_d \ldots\},$$

$$a \in \{0 \leq a_L, a_1, a_2, \ldots, a_H \leq 1\},$$

$$b \in \{0 \leq b_L, b_1, b_2, \ldots, b_H \leq 1\},$$

$$c \in \{0 \leq c_L, c_1, c_2, \ldots, c_H \leq 1\},$$

$$d \in \{0 \leq d_L, d_1, d_2, \ldots, d_H \leq 1\},$$

$$\ldots,$$

$$f_1(a, b, c, d, \ldots) \equiv a+b+c+d+\ldots -1=0,$$

$$f_2(a, b, c, d, \ldots) = 0.$$

$$\ldots,$$

$$f_M(a, b, c, d, \ldots) = 0.$$

It is important to note that, because the composition variables defining $\Omega_I$ must be non-negative and must also satisfy the normalization constraint, $f_1 = 0$, $\Omega_I$ is necessarily a finite space—that is, it has a finite hyper-volume. Consequently, it is possible to approximate $\Omega_I$ by discrete sampling with any desired accuracy by $\Omega_{ID}$ while maintaining the size of the set $\Omega_{ID}$ to be finite (as long as the exact reconstruction of $\Omega_I$ or any part of its nontrivial subspace is not required). Indeed, this approximation makes sense in the context of materials science, where a real world composition space is intrinsically discrete and the notion of mathematical continuity is itself an approximation. Because $\Omega_{ID}$ is finite, it can be mapped onto a two-dimensional surface (or even a one-dimensional space). The issue is how to do so in an efficient way.

One possible sampling scheme is uniform sampling, defined as $$\Delta \equiv \{A_a B_b C_c D_d \ldots\},$$

$$a = a_L + k_a \Delta a,\ k_a \in [0, n_a],\ \Delta a = (a_H - a_L)/n_a,$$

$$b = b_L + k_b \Delta b,\ k_b \in [0, n_b],\ \Delta b = (b_H - b_L)/n_b,$$

$$c = c_L + k_c \Delta c,\ k_c \in [0, n_c],\ \Delta c = (c_H - c_L)/n_c,$$

$$d = d_L + k_d \Delta d,\ k_d \in [0, n_d],\ \Delta d = (d_H - d_L)/n_d,$$

$$\ldots,$$

$$f_1(a, b, c, d, \ldots) \equiv a+b+c+d+\ldots -1=0,$$

$$f_1(a, b, c, d, \ldots) \equiv a+b+c+d+\ldots -1=0,$$

$$f_2(a, b, c, d, \ldots) = 0,$$

$$\ldots,$$

$$f_M(a, b, c, d, \ldots) = 0.$$

In this scheme, sampling precision is determined by sampling parameters, $n_a$, $n_b$, $n_c$, $n_d$, etc., in combination with range parameters $a_L$, $a_h$, etc. It should be noted that none of these sampling parameters need be identical—that is, sampling accuracy can be varied with respect to the corresponding component. The sample set, $\Delta$ (sometimes called a "basket" herein) is a collection of all the points.

Note that $a_L$, $b_L$, $c_L$, $d_L$, etc., are constants for all the points in $\Delta$, corresponding to uniform distribution of the relevant species in $\Delta$. These constants can be discarded by a suitable redefinition of the variables a, b, c, d, etc. and will be dropped in the following. Furthermore, $\Delta a$, $\Delta b$, $\Delta c$, $\Delta d$, etc., can be redefined as the units of the quantities of the corresponding species, and, with this understanding, they can also be dropped from the expression. With these treatments, $k_x$, can be replaced with x, to yield the following expression $$\Delta_u = \{A_a B_b C_c D_d \ldots\},$$

$$a \in [0, n_a],\ b \in [0, n_b],\ c \in [0, n_c],\ d \in [0, n_d],\ \ldots,$$

$$f_1(a, b, c, d, \ldots) = 0,\ f_2(a, b, c, d, \ldots) = 0, \ldots,$$

$$f_M(a, b, c, d, \ldots) = 0.$$

where a, b, c, d, etc., refer to the amount of the corresponding species in the corresponding unit.

In general, the basket need not be confined to a regular lattice of points. One may envision, for example, extracting a random sample from a given basket by selecting N random elements of the basket without replacement. This leads to a uniform random sample of the space described by the original basket. Several such samples can also be generated by subsequent extractions using, for example, a different random sequence. Other extraction algorithms can be employed, such as low discrepancy sequences, regular sequences etc. These will lead to different samples of the same space.

Tools, such as devices 140, can be used to apply parameters, including components, to regions in a library. Generally, devices 140 prepare libraries of materials by successively delivering components to predefined (i.e., known) regions on a substrate. In one embodiment, for example, a first component of a first material is delivered to a first region on a substrate, and a first component of a second material is delivered to a second region on the same substrate. Thereafter, a second component of the first material is delivered to the first region on the substrate, and a second component of the second material is delivered to the second region on the substrate. Each component can be delivered in either a uniform or nonuniform fashion to produce either a single stoichiometry or, alternatively, a large number of stoichiometries within a single predefined region. Components can be delivered in any convenient form, including, for example, as liquids, films, or lattice or superlattice structures. The process is repeated, with additional components, to form an array of components at predefined regions on the substrate. As explained below, components can be sequentially or simultaneously delivered to predefined regions on the substrate using any of a number of different delivery techniques. Optionally, the components delivered to one or more predefined regions on the substrate can be reacted (e.g., by the application of external parameters such as heat or pressure, or by other processes such as simple diffusion).

Devices 140 deliver a small, precisely metered amount of each component to each region with a known or measurable accuracy. This may be accomplished using a variety of delivery techniques, either alone or in combination with a variety of masking techniques. For example, thin-film deposition techniques in combination with physical masking or photolithographic techniques can be used to deliver components to selected regions on the substrate. More particularly, sputtering systems, spraying techniques, laser ablation techniques, electron beam or thermal evaporation, ion implantation or doping techniques, chemical vapor deposition (CVD), as well as other techniques used in the fabrication of integrated circuits and epitaxially grown materials can be applied to deposit highly uniform layers of components on selected regions on the substrate. Components can also be dispensed in the form of droplets or powder by conventional liquid-dispensing systems such as micropipetting apparatuses or ink-jet printers. By varying the relative geometries of the mask, target and/or substrate, components can be deposited within each predefined regions on the substrate or, alternatively, over all of the predefined regions on the substrate. These techniques can be used in combination with masking techniques to ensure that components are being delivered only to the regions of interest on the substrate.

The method by which a tool addresses different regions in the experiment lattice (e.g., wells, spots, etc.) is itself a parameter that can define a material, and is one way to differentiate between synthesis methods. While some tools address each site serially, other tools address several sites in parallel. Serial addressing offers maximum flexibility and diversification, because the amount of the parameter applied to any site in the lattice is uncorrelated with the amount applied to any other site. However, serial methods can be too slow for large numbers of sites.

Addressing sites in parallel can yield significantly greater throughput rates. For example, if an experimental design requires annealing 20,000 sites at 100° C. for 10 minutes, it is much faster to do all the sites at once, rather than each site sequentially. However, parallel addressing implies correlation between sites: whatever parameter is applied, it is applied equally to all sites. In the above example, parallel annealing might be practical if all 20,000 sites are on the same substrate. If the 20,000 sites are on 1000 different substrates, and the other points on any given substrate cannot be annealed, parallel addressing is less useful.

Thus, parallel addressing requires "arranging" samples in such a way that the maximum number of sites can be addressed at the same time by a given process. In the context of library-by-library processing, application of a parameter to an entire library simultaneously can be considered "completely" parallel (for that process step). By extension, application of the parameter to part of the library can be considered "partially" parallel, in that several sites are addressed in parallel, while other sites are not addressed. Thus, a "parallel efficiency" figure of merit (PE) can be defined as the ratio of sites addressed in a given step (Ns) to total sites addressable (N; in this example, N=number of sites on the library, or by extension, N=number of sites in the entire study)

$$PE = N_s/N$$

In the limit PE=1, the process is applied to all sites equally. In the limit of PE=1/N, the process is reduced to serial addressing.

The objective of any parallel process is to maximize PE: any step should be applied to the maximum number of sites. However, combinatorial libraries typically require diversity (i.e., differences between materials), so it is not often useful to create N duplicates of the same site. Thus, PE=1 is rarely achieved for all process steps.

Parallel addressing of sites can be achieved in a variety of ways for a variety of parameters, and can describe any process by which a parameter is applied to multiple sites simultaneously, without independent control over individual sites. Spray deposition of chemicals, sputtering of metals, illumination by light, or exposure to radiation are just some examples of processes that can be applied in parallel. For any of these processes, application is a description used here to mean "exposing a site to the process for a controlled time". Masking a site from the process is used here to mean "preventing the site from being exposed to the process". Parallel addressing is not limited to the actual process step that creates the material at a site on a library. For example, a batch annealing process that can simultaneously address 5 substrates might be optimized by an arrangement that fills sets of 5 substrates with sites to be annealed under identical conditions; in this sense, the libraries (and by extension the sites) are addressed in parallel by the annealing. In another example, a deposition tool might only accommodate 6 precursor solutions per synthesis run, with each precursor reservoir sufficient for 3 libraries. Sites could potentially be arranged on the libraries in such a way that all precursor reservoirs are depleted at roughly equal rates. One skilled in the art can easily think of many processes that can be described as forms of parallel addressing, each of which could have configurations that are more or less efficient.

One way to maximize PE for any process step is by arranging sites in such a way that the fewest number of sites are masked at any given time. However, synthesis typically takes place through many process steps—deposition of one component, deposition of another component, heat treatment, exposure to gases, etc. An arrangement of sites that is optimal for one process step might be sub-optimal for another process step. Thus, PE must be maximized subject to the constraints of all relevant process steps. By extension, the method of diversity implementation (e.g., how and when to perform any process step) can also be chosen in a way that maximizes PE.

In one implementation, system 100 performs a method for arranging sites in a fashion that maximizes PE for all process steps. This is achieved by describing the constraints of the process steps in an analytical fashion, creating a plurality of site arrangements, and choosing the arrangement that is most efficient. While this method can be applied to any parallel process that can be described in these terms, the following example illustrates the method in the context of the physical vapor deposition of a high-dimensional (composition) library.

One example of a device for preparing a library is illustrated in FIGS. 3A–C, which shows portions of a thin film physical vapor deposition (PVD) tool 300 for depositing a material using known techniques, such as pulsed laser deposition or sputtering by radio frequency waves. PVD tool 300 deposits material onto a substrate 310, which can be rotated relative to PVD tool 300. A mask 320 (which may be composed of polymers, plastics, resins, silicon, metals, inorganic glasses, or other suitable materials that will be readily apparent to those of skill in the art) is superimposed on substrate 310. Mask 320 includes multiple perforations (e.g., circular holes) 330 that define an array of locations on substrate 310, onto which deposition will take place. PVD tool 300 includes a source 340 of the material to be deposited and a pair of shutters 350 interposed between the substrate 310 and source 340. Shutters 350 can be positioned relative to substrate 310 to define a set of locations (e.g., a row or rows) in which the deposition will take place, as illustrated in FIG. 3C.

In general, a scientist using PVD tool 300 is interested in generating a library including compositions that include multiple elements. To that end, the scientist mixes elements by sequentially depositing each element onto the substrate using PVD tool 300. Each element can be deposited in varying molar compositions by varying the number of deposition steps (e.g., by depositing a given element multiple times) or the relative rate of deposition between deposition steps.

This particular mask/shutter combination implies a set of constraints on the deposition process. The shutters can only block a portion of the mask, leaving a whole set of rows exposed to the beam. Thus, for a given shutter configuration, an entire row or column of positions on substrate 310 is exposed to the same flux of deposited material. As a result, individual library elements are not separately addressable on substrate 310; instead, they must be addressed on a row-by-row or column-by-column basis.

System 100 maps a set of composition space points $\Delta_u$, onto the experiment lattice using one or more instances of a mathematical construct that will be referred to in this specification as a pattern. A particular pattern instance represents an individual step in the synthesis method—the delivery of a material to one or more regions of the experiment lattice—and must therefore be conformable to the synthesis methods used in library preparation (or vice versa). A pattern must also be superimposable on the experiment lattice, which represents locations at which the library is to be prepared.

A pattern is thus a slice of a parameter with a thickness representing a quantity of the corresponding parameter it represents. A collection of patterns is a set, symbolized as $\Sigma$, which will be referred to as a configuration in this specification. A configuration $\Sigma$ is mapped to an experiment lattice by stacking all of the patterns onto the lattice (in this context, "stacking" is used in a general sense, and is not necessarily limited to placing one thing on top of something else).

A pattern has one or more than one attributes. One or more than one of these attributes can be variable—i.e., it can possess various values. Two patterns are identical to each other if and only if all their respective attributes are identical. Two configurations are identical to each other if and only if all the aspects of the two configurations are identical. A collection of all the possible or allowed configurations is a set, symbolized as S, which will be referred to as the configuration space in this disclosure. Thus, $\Sigma \in S$.

Mapping of a configuration $\Sigma$ results in a set of points in the parameter space and establishes a one-to-one correspondence of this set of points with the points of the lattice. This set is symbolized as $\Gamma$, and is referred to as a trial. Therefore, we have $$\Gamma = f(\Sigma \in S)$$

That is, $\Gamma$ is a function of configuration $\Sigma$ belonging to S.

Accordingly, mapping a set of points in composition space to a two-dimensional lattice amounts to a search for a particular configuration $\Sigma_b$, that satisfies the condition $\Delta_u \subset \Gamma_b = f(\Sigma_b)$ (i.e., $\Delta_u$ is a subset of $\Gamma_b$). If the search yields two non-identical configurations, $\Sigma_b$ and $\Sigma_{b'}$, that both result in the desired mapping (i.e., they both contain the same $\Delta_u$), these may be distinguished by selecting the configuration, e.g., $\Sigma_b$, that is judged "better" or more desirable because, e.g., it contains less patterns (and therefore costs less to construct), its patterns are easier for implementation by a particular device, and/or it has some other desirable feature or is judged better by other figures of merit, etc. As these discussions may suggest, a strategy to solve the mapping problem must include: (a) establishing (or creating or otherwise obtaining) a set of parameter space points, $\Delta_u$; (b) establishing (or creating or otherwise obtaining) a configuration space, S, (c) establishing (or creating or otherwise obtaining) a set of figures of merit; and (d) executing trials and judging the results against the figures of merit.

As will be discussed below, a configuration space S can be huge, making it practically impossible or at least very difficult for a human scientist to identify a specific configuration $\Sigma$ that satisfies a given figure of merit; computers or other calculation devices are much more suited to such tasks. In order to enlist the help of such devices, one must translate the set of figures of merit into a quantifiable function—an objective function, symbolized as $\chi$ (which may also be referred to as a cost function in the following discussion). The process of constructing an objective function is described next.

To map $\Delta_u$ to points in a lattice, it follows that $$\chi(\Gamma) = f_a(\Gamma \cap \Delta_u),$$

where $f_a$ is the number of (or a function of the number of) overlapping points between the two sets, $\Delta_u$ and $\Gamma$, for example the percentage of (or a function of the percentage of) the points in $\Delta_u$ captured by $\Gamma$ versus the total number of the points in $\Delta_u$.

If two configurations can both fulfill the mapping task while one of them includes less patterns, then the configuration requiring less patterns might preferred because it may be more efficient to prepare. Thus, $$\chi(\Gamma) = f_a(\Gamma \cap \Delta_u) + f_b(\Gamma),$$

where $f_b$ is a function of the number of the patterns contained in Γ. Similarly, if a configuration satisfies the mapping on a smaller substrate, then it may be preferred over configurations that would require larger substrates. Thus, $$\chi(\Gamma)=f_a(\Gamma \cap \Delta_u)+f_b(\Gamma)+f_c(\Gamma,L),$$

where $f_c$, is a function of the size of the lattice required by Γ.

Not all the criteria need be weighed equally. Thus, one term can be emphasized more heavily than others, depending, for example, on the nature of the problem being investigated or other factors. Weighting factors can be introduced explicitly as follows:

$$\chi(\Gamma)=w_a f_a(\Gamma \cap \Delta_u)+f_b(\Gamma)+w_c f_c(\Gamma,L),$$

For example, one might sometimes be willing to accept a less perfect mapping (Γ including less than all the points in $\Delta_u$) in exchange for a configuration requiring the construction of fewer patterns. These weighting factors can be used to express this preference.

This illustrates how an objective function can be constructed incorporating various figures of merits and other considerations. The particular functions are not critical to the systems and methods described herein; those skilled in the art will recognize that other entities can be constructed to serve the same purposes without departing from the spirit of this disclosure. Several specific applications will now be described.

Consider first a single-pair dynamic shutter masking scheme as described above and shown in FIG. 3A. Such a scheme can efficiently produce a gradient or gradient-like profile. To take advantage of this capability, all patterns in a trial Γ can be grouped according to their associated parameters—for instance, all patterns representing component A may be grouped in one group, all patterns representing component B in another, and so on. All patterns in a given group can be further categorized into subgroups according to, e.g, their orientation with respect to the experiment lattice, so that all patterns within a subgroup are substantially parallel to each other. One can then examine the profile of each subgroup and count the number of gradient or gradient-like profiles as illustrated in FIG. 4, where subgroup A includes one gradient and subgroups B and C includes two gradient-like profiles each. These numbers are to summed obtain the total number, which is substituted into function $f_b$.

In one embodiment of dynamic shutter masking systems (described, for example, in U.S. Pat. No. 6,045,671), the system includes multiple sources that can be simultaneously activated to deliver different species onto the same exposed area of a substrate at one time.

To take advantage of this functionality, it may be beneficial to examine all groups and subgroups to identify (and count) profiles that are fully or partially overlapping. The total number of such profiles can be incorporated into the objective function (with the appropriate weighting factor) to capitalize on this arrangement.

Where it will provide some benefit to the particular application in question, patterns can be combined or decomposed, e.g., to simplify optimization or coding. Thus, in the liquid dispensing system described earlier, the liquid delivery tips form, e.g., a one-dimensional array. Because each action of the system corresponds to a linear pattern having a width of one unit (which presumably equals the unit spacing of the associated lattice), it may make sense to decompose all patterns into patterns having one unit width. Conversely, one can also essentially combine a set of neighboring, unit-width patterns to form a single pattern (assuming, e.g., they are located adjacent to each other with no overlap).

In implementations involving intensive parameters such as temperature, a temperature parameter can be incorporated in the configuration by defining all patterns to have unit "width" and variable "thickness" in the temperature attribute, since temperature is relatively easy to control. By further restricting each pattern to one orientation corresponding to the heater arrangement, temperature can be mapped as any of the extensive parameters discussed above.

FIG. 5A illustrates a gradient profile 500 representing uniform sampling of a component in, e.g., the generation of a binary or ternary library using a single pair shutter masking scheme as described above. Since each step in the profile has exactly the same step height, corresponding to one unit amount of the species as indicated, the gradient profile can equivalently be viewed as shown in FIG. 5B. That is, a stepwise gradient profile 500 is equivalent to a particular stacking 510 of a particular set of patterns having particular widths but identical thickness on a two-dimensional surface. Without losing generality, it is further noticed that the sequence of a stacking is not an essential feature at this stage.

As discussed above, a material can be analogized to a point in a multidimensional parameter space, with dimensions defined by a set of parameters. Most, if not all, parameters can be classified as either extensive or intensive parameters. Extensive parameters include, for example, the amount of a component species, weight, volume, heat, time, etc. By contrast, intensive parameters are not additive and include, for example, temperature, pressure, field strength, kinetic energy of an ion beam, etc. While variables in composition space are all extensive parameters, variables in process parameter space can be either extensive or intensive. Therefore, process parameter space can be further divided into two subspaces, one including only variables that are extensive in nature, another including only intensive variables.

For the purposes of this specification, the most important characteristic of an extensive parameter is its additivity. One liter of water added to one liter of water give two liters of water; conversely, two liters of water can be obtained by adding one liter of water to one liter of water. Additivity is the foundation of the pattern model. A parameter—e.g., the amount of a given component—is sliced into multiple quanta, each corresponding to a pattern, and the patterns are stacked together to realize the parameter, e.g., the desired amount. Stacking is addition.

The pattern model is not limited to mapping composition space to a two-dimensional physical surface. Rather, the methodology is applicable to the mapping of any extensive parameters, as evidenced by the examples described earlier. In practice, it is often possible to transform an intensive parameter to an extensive one. For example, temperature is an intensive parameter. The effect on a material of experiencing 500K twice is usually not the same as experiencing 1000K once. However, it is possible to devise a system such that temperature experienced by a material is a function of, and is therefore controlled by, the heat it is exposed to. Heat is an extensive parameter, and is therefore additive. In this way, a temperature parameter is transformed to a heat parameter. Note also that in certain cases, some intensive parameters can also be incorporated into the mapping scheme, as illustrated in the examples given in this disclosure.

As discussed above, it can often be difficult or impossible to map a high-dimensional composition space, including $\Delta_u$, onto a two-dimensional physical surface using conventional schemes, which typically impose too many restrictions on the individual patterns, as well as the relationships among the patterns. If these restrictions are relaxed or removed, it becomes possible, especially considering that $\Delta_u$ is a finite set, to map the composition space $\Delta_u$ onto a two-dimensional physical surface.

These insights suggest a solution for the mapping problem, based on the following assertions:

1: Any library residing on a physical surface can be viewed as a superimposed set of patterns (a configuration).

2: Any $\Delta_u$ can be mapped onto physical surface by an appropriate set of patterns.

FIGS. 6A–E illustrate a series of masking systems suitable for implementation (either individually or collectively) in a device 140 such as a PVD device 300. As shown in 6A, the system 600 includes a pair of shutter masks 605 capable of forming rectangular patterns on a substrate 610 supporting a square or rectangular lattice 615. The shutters 605 can be configured to move independently or in concert (as identified by the arrows adjacent to shutters 605). Substrate 610 can be configured to rotate with respect to its center or origin. Thus, the space between shutters 605 defines a pattern 620 on substrate 610, exposing a portion of the lattice to the delivery of a component or components, or other physical or chemical operations. In this system, pattern 620 has at least the following attributes: (1) a width; (2) a location (relative to lattice); and (3) if device 140 is configured for relative rotation of substrate 610 and shutters 605, an angle. Due to the nature of the lattice, each of these attributes is a discrete variable.

Similarly, FIGS. 6B and 6C illustrate shutter pairs 625 and 640, configured to form right-angle patterns 630 on a substrate 635 and 120°-angle patterns 645 on a substrate 650, respectively. Such patterns can be advantageously employed to accommodate particular symmetries contained in certain composition spaces $\Delta_u$. FIG. 6D illustrates a masking system involving two pairs of shutters 655, that are configurable to form rectangular patterns 660 on a substrate 665, as discussed in U.S. Pat. No. 6,045,671, which is incorporated herein by reference for all purposes. Because all four shutters 655 can move independently, the system can form any rectangular pattern anywhere on substrate 665.

FIG. 6E illustrates a masking system 670 for generating more complex patterns on a substrate 675, which masking system may be useful for composition spaces $\Delta_u$ having specific inherent symmetries. A shadow mask 680 has a set of predefined perforations or openings 685 configured to overlap with individual lattice sites when mask 680 is superposed on substrate 675. Mask 680 can move independently along one or two directions as indicated by the arrows, and optionally can be configured to rotate relative to the substrate. Openings 685 expose a set of points of the lattice to the delivery of a component or components, or other physical or chemical operations. In one implementation, shadow mask 680 moves in one direction to create a series of pattern-instances. System 670 further includes a mechanism to automatically feed and remove different shadow masks 680 as needed, as disclosed in U.S. Pat. No. 6,004,617, which is incorporated by reference herein for all purposes.

The set of points exposed by shadow mask 680 corresponds to a pattern having at least the following attributes: (1) a number of openings; (2) a set of spatial coordinates of the openings (relative to each other); (3) a location of the shadow mask (relative to the substrate); and (4) if device 140 is configured for relative rotation of substrate 675 and mask 680, an angle. Again, due to the nature of the lattice, each of these attributes is a discrete variable. Note that the shape of the openings is not essential. Those skilled in the art will recognize that many other possible masking systems can be constructed and used in the systems and methods disclosed herein. Although these examples illustrate the features of a pattern in the context of particular masking systems, the patterns employed in the systems and methods described herein are not limited to masking/opening schemes.

In essence, application of a pattern to the lattice (or vice versa) causes a predefined set of points in the lattice to experience some physical, chemical, or other type of interaction. This can include, for example and without limitation, receiving species (electrons, photons, atoms, molecules, other particles, liquids, powders, other aggregates), reacting with species, environmental interactions (thermal, electric, magnetic, and other fields, etc.), or combinations of these.

For example, a parallel liquid dispensing system can include a pump connected to an array of 16 tips. The library substrate might be a 16×16 well plate situated on a rotatable stage. Stock solution of desired components are maintained in a set of reservoirs available to the tip array. The array is moved to a reservoir, where the pump aspirates some amount of the solution. The tip array is then moved over the plate so that the tips are aligned with a row or column of wells in the plate, by some combination of translational movement of the tip array and rotational movement of the plate. When the tips are aligned with a desired set of wells, the pump dispenses the solution into the wells.

In this example, the tip array corresponds to a pattern, with a length of 16 spatial units, a width of one spatial unit and a "thickness" (or amount) that is variable and defined by the amount of solution aspirated and dispensed. The sequence of aspirating solution, moving to a particular row or column and dispensing solution into wells corresponds to is one action corresponding to the superposition of an instance of the pattern on the substrate. Space mapping and library synthesis are accomplished in a series of similar actions.

In another example, a 16×24 well plate is filled with a constant amount of solid or liquid species to be used as catalyst or reagent. The plate is placed onto a fixture (such as, e.g., an array of microfabricated hotplates as described in U.S. Pat. No. 5,356,756) having 24 heating elements extended along one direction, which can be controlled individually. The plate can be rotated relative to the fixture so that either its rows or columns are aligned with the heating elements. The assembly resides in a pressure-controlled chamber, into which various gases or vapors can be introduced. The plate can further be transported (e.g., under inert atmosphere, if necessary) to neighboring systems for analysis as desired. At the start of a process, the loaded plate is introduced into the chamber and a row or rows (or a column or columns) are aligned with the heaters. The system is evacuated or flashed with inert gas (initialization). A prescribed gaseous species is then introduced into the chamber. The heaters are activated to a set of prescribed temperatures (heating can also occur before gas introduction). Each heater is held at a specified temperature for a specified period of time and then turned off. The system is then cleaned and ready for the next action. In this application, a group of patterns is realized in a single action, and the physical attributes of the pattern can include, for example, the reaction time at a specific temperature, the temperature for a specific time duration, the amount of the products produced under the given conditions, or various combinations of these and other considerations.

In still another example, the substrate is an 8×8 electrochemical cell array, which is placed onto a fixture having 8 rows of electric contacts. As described above, the cell array can be rotated so that either its rows or columns are aligned with the electric contacts, so that the cell array can be activated and controlled row-wise or column-wise as desired. As in the above example, in this application, a group of patterns is realized in a single action, and the physical attributes of the pattern include reaction, product, voltage, current, and other process parameters, depending on the specificity of the experiment. Note that the system could also be combined with another synthesis process, such as a liquid dispensing system as described above to enable the preparation of more sophisticated combinatorial libraries.

The previous discussion assumes that the parameter space is uniformly sampled to create $\Delta_u$, which is an approximation of the parameter space of interest. Those skilled in the art will recognize, however, that in some cases non-uniform sampling schemes may yield better results. Thus, for example, random sampling may be preferable for sampling some composition subspaces. A truly random sampling having a finite number of samples will inevitably leave some relatively large voids in the parameter space. To avoid this (generally) undesirable result, it is thus required that: (a) the number of samples within a hyper volume (with prescribed size and shape) should be essentially constant; (b) the samples within the hyper volume should be distributed in random fashion; (c) this should hold true regardless of where the hyper volume is placed within the parameter space of interest.

In one way to satisfy these requirements, a target basket, $\Delta_u$, is identified by uniform sampling of the parameter space of interest, and the "best" (or most acceptable) configuration is identified as described herein. One might then introduce one random number per each slab in the configuration so that the thickness of a slab becomes 1+r, where r is a random number uniformly distributed in (−1, +1) or smaller interval per the prescription of the hyper volume.

For most systems (e.g., chemical systems, materials, devices, etc.), the order of events is at least as important, if not more, as the events themselves. For example, in most organic and biological materials, structure is determined by the sequence in which individual components incorporated into the material. DNA, for example, is a combination of just four species (i.e., A, T, G, and C), but because DNA's properties derive from the sequence in which those species are combined, it is not possible adequately to represent a given DNA merely as points in a four-dimensional composition space. Similarly, electronic devices often involve materials—such as GMR heads or magnetic storage media, etc.—that include multi-layered structures. In such systems, the material used in each layer, its thickness, the number of layers, the order of stacking, and the like, are all important in determining the ultimate function or performance of the system. Likewise, in the synthesis, manufacturing, or production of chemicals, materials, devices, etc., process almost always plays essential role. With this notion, also with the slab model in mind, a parameter space can be perceived as an event space that includes all the events of relevance or interest except happenstance of events. To take these considerations into account, one can expand the notion of a parameter space to include the order of all possible events (or at least all events of interest), yielding what can be termed a sequence space, defined on the associated parameter space. The essence of sequence and sequence space is "order", which may or may not have direct association with how events actually occur in real time. For the purposes of this specification, time is considered an extensive parameter in parameter space, referring to, but not necessarily limited to, the duration of an event.

The methods and apparatus described herein can be applied to the combinatorial exploration of sequence space by expanding the definition of $\Delta_u$ to include (or in certain applications to be equal to) sequence space. Because sequence space is, by definition, discrete and, for any practical purposes, finite, $\Delta_u$ remains discrete and finite as well. In such implementations, a pattern can be considered to represent an event, just as patterns also implementations, a pattern can be considered to represent an event, just as patterns also represent components and process parameters. With such treatment, mapping sequence space is equivalent to mapping parameter space in terms of pathways and/or workflow.

Practical considerations dictate that all lattices be of finite size, whether they be one-, two- or three-dimensional lattices. On the other hand, a complete mapping is only possible where the size of the lattice (i.e., the number of the points in the lattice) is no smaller than the size of $\Delta_u$. In practice, the lattice is often required to be larger than the target basket (depending, e.g., on the complexity of $\Delta_u$ and the details of the system in question). However, for large or even moderately-sized target baskets, available substrates are typically smaller, often significantly so, than required, making it necessary to use multiple substrates, and therefore multiple lattices. This can be accomplished by expanding the definition of a configuration to include multiple lattices by simply adding to each pattern an attribute (either constant or variable, depending on the particular application) that identifies one or more lattices associated with the pattern.

In such implementations, multiple lattices used in a given configuration need not necessarily share the same characteristics. The use of different types of lattices in one configuration can be advantageous, for example, in capitalizing on symmetries inherent in $\Delta_u$. Furthermore, system 100 can incorporate different types of substrates served by different synthesis devices to implement such mappings, or can process individual substrates using more than one kind of synthesis device.

From a mathematical perspective, including excess points in the experiment lattice (i.e., more points than occur in the target basket) is redundant. As a practical matter, however, it may often be beneficial to have more (even substantially more) points in the experiment lattice than are included in the target basket $\Delta''$. This not only simplifies the task of finding a mapping, but also provides additional information that can be important in execution—for example, in diagnosis, quality control and the like. Furthermore, when a random sampling scheme is used, excess points become part of the statistical pool and are not even theoretically redundant.

The task, then, of mapping $\Delta''$ to a lattice or lattices is to search configuration space to find a configuration or a set of configurations that is acceptable, better, or the best, judged by an objective function—in other words to perform an optimization process. A variety of such optimization procedures are known, some of which will be described in more detail below; those skilled in the art will recognize several that can be used to for the purposes disclosed herein.

As discussed above, configuration space S is discrete and finite. More specifically, it is of, or can be converted to, integer type, which is advantageous for computer or other calculating devices. On the other hand, derivative-based optimization procedures (explicitly or implicitly) may not be able to utilize this advantage fully and may not be adapted directly without modifications.

One such procedure is the well-known genetic algorithm (GA) as an optimization tool for the task. While the procedural details of GA are generally known, the following discussion illustrates the object encoding process, one of the key steps in GA.

In GA, an object is represented by a string of bits (a bit sequence). Objects are encoded to establish relationships between the bits and the attributes of the object the string represents. For the purposes of this example, assume the hypothetical mapping of an entire four-dimensional composition space to a single square lattice using simple rectangular patterns. Assume also that we wish to sample the composition space with 15 intervals per each component. Thus, each pattern's thickness attribute is expressed in units corresponding in real physical terms to ~6.7% mole (100%/15). The total number of points in $\Delta''$ is calculated according to the following $$Size(\Delta_u) = C_{M+N-1}^{N-1} = \frac{(M+N-1)!}{M!(N-1)!}$$

where, M is the number of intervals (here, M=15); N the number of ingredients (here, N=4). Thus, in this example, the size of $\Delta_u$ is 816. Hence one might like to use a 32 by 32 lattice yielding 1024 lattice points. Note that the $\Delta_u$, includes all the points for quaternary, ternary, binary, as well as single elements. A mapping limited to the quaternary points could be calculated according to the following:

$$Size(\Delta_u) = C_{N-1}^{N-1} = \frac{(M-1)!}{(M-N)!(N-1)!},$$

yielding a size of just 364.

We first construct a representation for a pattern. Since there are 4 components involved, 2 bits of a string are used to define the pattern's component attribute. The pattern's width is defined with 6 bits (since a pattern can be as wide as 63 lattice points along the diagonal). Two bits are required to define the pattern's orientation (since there are 4 possible orientations of a pattern with respect to the lattice. Finally, 6 bits are required to define the distance of the pattern from the lattice origin (placed, e.g., at a corner of the lattice)— e.g., the number of rows or columns, or diagonal rows or columns, counting from the origin to a designated edge of the pattern. Thus, in this example a pattern can be described with a total of 16 bits (i.e., 2 bytes).

To construct a configuration (the GA object), general mathematical considerations suggest that for M=15, each component will require at least 8 patterns, suggesting that a configuration can be represented by a string at least 64 bytes (i.e., 512 bits) long (2 bytes per pattern, 8 patterns per component, 4 components total). Consequently, the corresponding configuration space contains $2^{512} \approx 1.34 \times 10^{154}$ possible configurations. In practice, a longer string will be required—typically twice as the minimum—although the strings will be allowed to shrink during their evolution. Thus, the optimization will require a typical string that is 128 bytes long, such that the size S is $2^{1024} \approx 1.8 \times 10^{308}$. As this example demonstrates, configuration space can be enormous for even a relatively simple task, making an exhaustive search difficult or impossible even with the best available computers.

FIG. 7 illustrates a method 700 of designing and preparing a high-dimensional library of materials on a two-dimensional substrate using system 100. The method starts when system 100 obtains a definition a subspace of interest in the parameter space (step 710) (for example, a set of desired compositions to be included in a library of materials as described above). In the following description, this subspace of interest will sometimes be referred to as a "target basket" or "desired basket". This target basket can reflect a set of materials to be analyzed for one or more desired properties, and can be derived from any convenient source, including, for example, an automated experiment design system such as that disclosed in U.S. Provisional Application No. 60/198,208, filed Apr. 19, 2000, which is incorporated by reference herein.

System 100 then obtains one or more patterns representing the attributes of device(s) 140 and one or more experimental lattices representing a substrate or substrates on which the library of materials is to be synthesized (step 720). In some implementations, the experiment lattice describes the physical constraints of the substrate. An experiment lattice can include, for example, a mathematical representation of the substrate including the substrate geometry (e.g., square, circular, triangular, etc.) and size (e.g., the number of rows and columns of a given size that will fit on the substrate). In one implementation, an experiment lattice is defined by the overlap of a mask with a substrate, where the mask identifies points in the experiment lattice as described above. The patterns include one or more device patterns describing the physical constraints of one or more devices 140. As described above, a device pattern can include a mathematical representation of fundamental constraints such as shape, complexity and boundary conditions describing the kernel process step of device 140, such as an array of points corresponding to a liquid-dispensing array, or a space or opening defined by a shadow mask or set of one or more masking shutters. The device pattern can be generic or specific to particular devices. In one implementation described above, a device pattern represents the shuttering geometries of an automated physical vapor deposition device, defining an area spanning rows of points in a substrate lattice. In one such implementation, a pattern can be uniquely identified by a combination of attributes including: (1) the identity of a component to be deposited; (2) a direction relative to the lattice (e.g., horizontal, vertical, positive diagonal, negative diagonal for square lattices, etc.); (3) an offset position of an edge relative to the lattice (e.g., for horizontal rectangles, the top or bottom edge; for vertical rectangles, the left or right edge, etc.); (4) a width, or number of rows that the pattern covers on the lattice; and (5) a thickness (in arbitrary integer units). As discussed above, these quantities correspond to physical operations capable of being implemented by device 140. The device pattern can be obtained from any convenient source, such as from a user or from memory. Alternatively, the device pattern can be implemented directly in library optimization program 130. In one implementation, the optimization program explicitly considers a plurality of lattices (and/or substrates) and the respective configurations that can describe a deposition process or other chemical or physical process. The optimization is then considered to take place simultaneously over the global set of patterns for all configurations.

Library optimization program 130 generates an initial candidate design, an "experimental basket" that in some sense approximates the target basket. To generate the experimental basket, library optimization program 130 generates a pattern set including multiple patterns, with varying values assigned to the pattern attributes, superposed onto the experimental lattice or lattices (step 730). Thus, for example, a configuration can include a plurality of overlapping patterns generated by randomly changing one or more attributes (size, shape, complexity, thickness, etc.) associated with other patterns in the set. As discussed above, each pattern in the configuration can represent, e.g., the delivery of one component (or one processing condition) to a point or points in the lattice.

In this example, each point in the experiment lattice is assigned a mixture of components (and/or process conditions or other parameters) determined by the patterns that overlap the lattice point. This mixture corresponds, for example, to a molar composition of component materials, and represents a point in composition space (with the set of points in the configuration making up the experimental basket). The state of a configuration can be described by a series of variables—e.g., the number of patterns in the configuration and their attributes, which library optimization program uses to calculate the composition of the experimental basket (step 740) and stores that composition for use in optimizing the configuration, as will be described below. A configuration is ordered and corresponds to a nominally unique set of compositions in the experimental basket.

In one implementation, the process of designing a library of materials containing a desired set of compositions amounts to identifying a configuration that defines an experimental basket containing all (which may or may not in fact be possible for a given set of desired compositions and a given lattice) or most of those compositions. In one implementation, library optimization program 130 performs step 730 by generating an arbitrary configuration. For a complex, higher-order design, such an arbitrary configuration will most probably not actually yield an experimental basket including each composition in the target basket.

From this starting point, library optimization program 130 optimizes the configuration on some figure of merit (step 750) by generating a broad range of configurations (changing pattern shape, size, number, complexity, deposition (i.e., pattern) order, lattice shape, size, number, substrate number, substrate order, thickness or other attributes as discussed above) and comparing the compositions calculated for various configurations with those in the target basket and optionally performing additional evaluations of the configuration, including, but not limited to, the order of application of the patterns. The details of this optimization process will be described in more detail below. After identifying one or more optimum configurations—for example, patterns sets whose compositions closely or exactly represent those of the target basket and/or whose synthesis requires minimum resources—library optimization program 130 outputs synthesis information describing the optimum configuration or configurations (step 760)—for example, in a format suitable for input into an automated library design program such as is described in U.S. application Ser. No. 09/420,334, filed on Oct. 19, 1999, which is incorporated by reference herein.

Optionally, this information can be output in a format compatible with data visualization software such as Mathematica software available from Wolfram Research. Using such software, a user can visualize the optimum configuration or configurations, as illustrated, for example, in FIG. 8A, which depicts an configuration 800 of patterns 810 for synthesis by an synthesis tool such as PVD tool 300. In one implementation, the automated library design program incorporates the synthesis information, as well as additional information such as molecular weights, densities, superlattice requirements and the like, to generate a recipe file containing instructions to guide tool 300 in the synthesis of a physical library embodying the optimum configuration (step 770). Optionally, the automated library design program can generate a graphical composition map 820 depicting the resulting library for display on output device 150, as illustrated in FIG. 8B, where, for example, each matrix element 830 represents one location in the library to be synthesized. This composition map can also be displayed using third party visualization software, such as Spotfire, as illustrated in FIG. 8C. Device 140 uses the recipe file to prepare a library incorporating compositions corresponding to the composition-space points identified in the optimum configuration (step 780), for example, using automated library design and synthesis methods and apparatus such as those described in U.S. application Ser. No. 09/420,334, filed on Oct. 19, 1999, and U.S. application Ser. No. 09/305,830, filed on May 5, 1999, both of which are incorporated by reference herein. The completed library can be submitted to further processing or analysis using high-throughput techniques, such as those described in U.S. Pat. Nos. 5,959, 297, 6,030,917 and 6,034,775, which are incorporated by reference herein.

Returning to the optimization process, library optimization program 130 can perform the optimization using Monte Carlo or other known techniques. In one implementation, library optimization program 130 begins by identifying a second configuration by changing one or more of the variables defining the initial configuration—for example, by changing the number of instances of a device pattern in the configuration (i.e., adding or subtracting one or more instances of the device pattern for a given component material), changing the component material for a given instance or instances of the device pattern, changing the direction, offset, width or thickness (or other corresponding attribute) for one or more instances of the device pattern, or by changing the order of the device pattern. A change in the configuration will result in a change in the composition of materials at one or more points in the experiment lattice (and therefore in the ultimate library of materials to be synthesized) or the sequence of the process applied. In one implementation, library optimization program 130 identifies a second configuration by introducing a random (or quasi-random) change in the configuration state.

As described above, library optimization program 130 compares the initial configuration and second configuration to determine, e.g., whether the second configuration more closely resembles the target basket (although library optimization program 130 can be configured to optimize on properties other than closeness of fit to the target basket, as will be discussed in more detail below). In one implementation, library optimization program 130 performs this comparison by calculating and comparing for each configuration a figure of merit (or cost function) that numerically represents how well a configuration solves the problem of arranging the set of compositions in the target basket onto the two-dimensional substrate, or a set of substrates.

In general, the figure of merit can. be expressed as the sum of terms that depend on external input (desired basket, geometrical constraints, number of substrates, relative weight parameters) and the current configuration:

$$FM = \sum_{i=1}^{N} w_i H_i(input, configuration),$$

where the $w_i$ are a plurality of relative weight parameters that determine the importance of each term in the sum, and $H_1$ (input, configuration) are a plurality of single-valued functions. These functions assume different values for different realizations of the configuration, including, but not limited to, the pattern geometries, the number of patterns and their order. The functions are designed to assume the lowest values for configurations that are understood to be "good". Such pattern sets may not be known a priori, but the functions can be devised to discriminate according to the desired features. Each term of the above equation may be devised to evaluate a given feature of the pattern set. The values of the weight parameters $w_1$ can be determined by trial and error.

Assume, for example, a desired basket DB of N different desired compositions. A given configuration corresponds to an experimental basket EB. The experimental basket includes a set of members equal to the number of locations defined by mask 220, and larger than the number of compositions in the desired basket.

In this example, the figure of merit can be represented as the sum of two terms:

$$FM = wD_b^2 + \mu(N_s - N_0),$$

where w is a weight parameter, $D_b^2$ is the basket term, $\mu$ is another weight parameter, $N_s$ is the number of equivalent patterns and $N_o$ is a target minimum number of patterns, used to make the two terms comparable. The first term is the result of the comparison between the DB and the EB, as described below, and the second term is an "insertion cost", that grows linearly with the size of the pattern set, and that tends to minimize the number of patterns needed to realize the DB. In this sense, $\mu$ is akin to a chemical potential. The terms of the above expressions should return the same value for the same input and parameter set. The calculation of these terms in this example is described next.

For a given configuration, library optimization program 130 measures the first term, $D_b^2$, as follows. First, library optimization program 130 searches the desired basket for composition space points that occur exactly in the experimental basket. Library optimization program 130 flags any points that occurs in both the DB and the EB and ignores those points in the following steps. If all DB points occur the experimental basket, library optimization program 130 flags the current configuration as "Qualified". In this example, more importance is given to the condition that the EB match the DB, but this need not always be the case.

Next, if some points in the desired basket do not occur exactly in the experimental basket, library optimization program 130 searches the EB for the closest match to each DB point. Again, library optimization program 130 flags any matched points and removes those points from the search. Library optimization program 130 defines the closest match based, for example, on the "distance" between the points, defined, for composition space points $P_1=(A_1, B_1, C_1)$ and $P_2=(A_2, B_2, C_2)$, as $D^2=(A_1-A_2)^2+(B_1-B_2)^2+(C_1-C_2)^2$. Library optimization program 130 searches the experimental basket based on the order of points in the desired basket, which is fixed by the input, thus ensuring that inexact matches are always assigned in the same manner. As a result, the association of a figure of merit for a given DB and configuration is unique.

Finally, library optimization program 130 calculates Db as the sum of all squared distances between inexactly matched points:

$$D_b^2 = \sum_i D_i^2.$$

Accordingly, if the experimental basket (i.e., the current configuration) includes all of the desired compositions in the target basket, the figure of merit will be very small (in applications where this term is emphasized). Conversely, if the experimental basket does not include many of the desired points, the figure of merit will be large. The term proportional to the number of patterns is used to discriminate between qualified configurations, to identify, for example, the qualified configuration using the smallest number of patterns (and therefore providing the most economical synthesis with device 140). The best value of the weights w and $\mu$ must be determined empirically, baaed, e.g., on trial optimizations on sample baskets. In general, a large $\mu/w$ ratio will frustrate the system by constraining the system to use only a small number of patterns. Conversely, a small $\mu/w$ ratio will lead to optimal DB coverage with very many operations.

The particular mathematical definition of the figure of merit is not critical. The definition provided above is simple and relatively easy to implement, essentially treating each point in the DB as a spring (harmonic term) with respect to a location on the substrate, and the association between points on the substrate and points in the desired basket being dynamic and adaptive. However, those skilled in the art will recognize that other figures of merit could be employed with similar results.

As discussed above, library optimization program 130 identifies the "best" configuration (e.g., in some cases the configuration that can be prepared by device 140 that most closely approximates the target basket) by optimization. The optimization can be carried out in a variety ways, using known optimization techniques. In the implementation described above for PVD tool 300, the problem reduces to the minimization of a function of many variables, with degrees of freedom corresponding to the number of patterns and the attributes of each pattern. Accordingly, in this implementation, library optimization program 130 can change a configuration by adding a pattern with valid random attributes, removing a randomly selected pattern, or randomly changing a randomly selected attribute of a randomly selected pattern. Each change in a configuration corresponds to a change of the figure of merit for the configuration.

In one implementation, library optimization program 130 implements a stochastic optimization process, such as Monte Carlo processes based on simulated annealing, parallel tempering or a combination thereof. Alternatively, library optimization program 130 can implement other optimization processes, such as the multidimensional simplex method, conjugate gradients, genetic algorithms or other known processes, as described, for example, in W. H. Press et al., "Numerical Recipes: the Art of Scientific Computing," 2nd ed., Cambridge Univ. Press, 1992 or Z. Michalewicz, "Genetic Algorithms+Data Structures=Evolution Programs," 3rd Ed., Springer, Berlin, Germany, 1996.

As those skilled in the art will recognize, a Monte Carlo process is a type of stochastic process that generates a sequence of configurations (here, a sequence of configurations) that make it both reversible—that is, at any time there is a non-zero probability that the process selects the inverse step and reverses the sequence—and ergodic—that is, in some sense, the sequence of configurations can never enter a cycle of finite length.

The Monte Carlo process is based on the notion of an "Update"—a change in the configuration of the system that is random and that depends only upon the current configuration (a Markov chain of configurations). In the implementation of FIG. 1 where device 140 is a PVD tool 300, an update is a change in the configuration that is chosen independently of the number of patterns in the configuration and the attributes of those patterns. An update can be accepted or rejected. An accepted move will change the state of the configuration, while a rejected move will leave the configuration unchanged but will nonetheless be considered part of the sequence generated by the algorithm.

The Accept/Reject step can follow any rule that satisfies the detailed balance condition:

$$P(A)W(A{\rightarrow}B)\mathrm{acc}(A{\rightarrow}B)=P(B)W(B{\rightarrow}A)\mathrm{acc}(B{\rightarrow}A)$$

where P(A) is the absolute probability that the configuration is in state A, W(A→B) is the probability to select B from A, acc(A→B) is the probability of accepting the update, and, likewise, P(B) is the absolute probability that the configuration is in state B, W(B→A) is the probability to select A from B and acc(B→A) is the probability to accept the reverse move.

If the update is state-independent and it follows detailed balance then the limiting probability distribution sampled by the stochastic process is P itself. It follows that in order to sample from the probability distribution P, configuration updates should proceed according to the detailed balance rule.

Library optimization program 130 samples a probability distribution, such as the Boltzmann distribution $$P_\beta(C) = \frac{\exp[-\beta H(C)]}{\sum_{\{C'\}} \exp[-\beta H(C')]},$$

which typically describes thermal equilibrium (although other probability distributions, such as the Tsallis distribution, can be sampled as those skilled in the art will recognize). Here C is the configuration, H is the figure of merit (FM above), and β is a selection parameter (usually associated with an inverse temperature). The denominator is a normalization factor, and, applying the detailed balance condition set out above, cancels out exactly on both sides of the equation. The sum extends over all possible configurations.

The transition matrix W(A→B) describes the update rule. If two states cannot be joined by a valid update, then W=0. Typically, one chooses a symmetric update rule, or $$W(A{\rightarrow}B)=W(B{\rightarrow}A)$$

and the transition amplitude also drops from the expression. Thus, for the Boltzmann distribution, the detailed balance condition reads:

$$\frac{\mathrm{acc}(A \rightarrow B)}{\mathrm{acc}(B \rightarrow A)} = \frac{\exp[-\beta H(B)]}{\exp[-\beta H(A)]} = \exp(-\beta \Delta H)$$

One choice for the update rule, the Metropolis Algorithm, provides that $$\mathrm{acc}(A{\rightarrow}B)=\min[1, \exp(-\beta\Delta H)],$$

and vice versa for the reverse move. If the change in the figure of merit between state B and state A, ΔH, is greater than 0, then the probability of accepting the move is exponentially small, while if ΔH<0 the move is always accepted. If ΔH=0 library optimization program 130 can be configured to adopt the new state, retain the old one or to use some other, predetermined method, such as a coin toss, to decide.

In one implementation, library optimization program 130 performs a parallel tempering method as illustrated in FIGS. 9 and 10. In this process, library optimization program 130 runs multiple concurrent Monte Carlo processes, each having a different value for a selection parameter β—for example, three processes A, B and C, having low, moderate and high β values, respectively. Library optimization program 130 begins the method by obtaining an initial experimental basket, for example, by generating an arbitrary configuration as described above (step 900). Library optimization program 130 calculates a figure of merit for the initial experimental basket, as described above (step 905). As the optimization proceeds, library optimization program 130 retains a record of the "best" (i.e., lowest H) configuration obtained in the process, which is the initial configuration at the start of the method (step 910). Library optimization process 130 obtains a number of simulations, N, which may, for example, be input by a user, retrieved from memory, or coded in library optimization program 130 (step 915). Library optimization program 130 then sets a selection parameter for each simulation (step 920). Library optimization program 130 then carries out the first round of updates by generating a new experimental basket for each simulation (step 925), and calculating a figure of merit for each new basket (step 930). If the figure of merit of a new basket is better (e.g., lower) than the recorded optimum (the YES branch of step 935), library optimization program 130 saves that new basket as the optimum (step 940). For each simulation, library optimization program 130 determines whether to accept the new basket by applying an acceptance rule such as is described above (step 945). If more updates remain in the round (the YES branch of step 955) (that is, if a predetermined number of updates has not been carried out for the current round), library optimization program 130 generates a new set of experimental baskets (step 960) and repeats steps 930 to 955. When no more updates remain for the current rqund (the NO branch of step 955), the round is over.

As discussed above, the processes are assigned differing selection parameters, which can be thought of as thermodynamic temperatures for each system. The low β system A possesses, on average, enough "energy" to pass most or all energy barriers (that is, all changes in the state of the configuration are readily accepted according to the acceptance rule), so that it can explore all possible states of the system essentially at random (given enough simulation time). By contrast, the high β system C does not, on average, possess enough "energy" to pass the acceptance threshold, and therefore mainly probes local energy minima. Accordingly, to gain the benefit of both the "coarse" resolution of high-energy (low β) and low energy (high β) Monte Carlo processes, after completing a round of updates (or at other predetermined intervals), library optimization program 130 proceeds to conduct a parallel tempering "swap" as shown in FIG. 10.

Library optimization program 130 gets the current experimental baskets for each of the N ongoing simulations (step 1000), and calculates a global figure of merit for the set of simulations—for example, by summing the individual figures of merit for each basket (step 1010). Library optimization program 130 then "swaps" configurations by selecting two baskets and exchanging the selection parameters of the selected states (step 1020)—for example, by swapping between systems having a low and intermediate β values, respectively. Library optimization program 130 recalculates the figures of merit for the new baskets (step 1030). As discussed above, if the figure of merit for any new basket is more favorable than that of the current optimum (the YES branch of step 1040), library optimization program 130 adopts that new basket as the optimum (step 1050). Library optimization program 130 calculates a new global figure of merit—for example, by summing the recalculated figures of merit (step 1060)—and determines whether to accept the swap using an acceptance rule such as that described above (step 1070). Library optimization program 130 then proceeds to the next round of updates, returning to step 900 but using either the current baskets produced in the preceding round of updates or the swapped baskets, depending on the result of step 1070.

Optionally, at the end of any given round (e.g., after conducting the "swap" described above) or at any other predetermined interval, library optimization program 130 performs a simulated annealing method 1100, illustrated in FIG. 11. This known technique further compensates for the difference in precision between high- and low-energy systems by iteratively proposing changes between "temperature" extremes defined for the system. In this method, library optimization program 130 gets a maximum and minimum temperature from, for example, user input or memory (state 1110). Library optimization program 130 retrieves the saved optimum basket (step 1130), and, in a process that stochastically simulates the slow cooling of a physical system, performs a series of updates between the temperature extremes. Starting at the maximum temperature (step 1140), library optimization program 130 generates a new basket (step 1150), and applies the acceptance rule as described above (step 1160), repeating this process for a predetermined number of updates at the maximum temperature (steps 1150–1185). After reaching the predetermined number of updates at that temperature (the YES branch of step 1180), library optimization program 130 decreases the temperature (step 1195), and repeats steps 1150–1185 at that temperature for the predetermined number of updates, decreases the temperature again, and so on until library optimization program 130 reaches the minimum temperature (the YES branch of step 1190), at which point the simulated annealing process is complete and library optimization process 130 proceeds to further processing, such as a next round of updates in FIG. 9. At the completion of the Monte Carlo process, system 100 outputs the synthesis information for preparation by device 140 as discussed above.

It should be recognized that in the practical sense (i.e., when actually making real materials) one might not be able to determine a priori the best way to sample a parameter space. A useful material might be discovered via inefficient sampling, while an ostensibly "optimal" sampling strategy can still miss useful materials. Lack of success (e.g., not finding the material with the target property) may not necessarily signify a poorly sampled parameter space, and success (e.g., finding the desired material) does not signify that the parameter space was optimally sampled. The ultimate goal is a new, useful material or process; the best sampling strategy is simply one that yields that goal with minimum resources.

One benefit of the methods and apparatus disclosed herein is the ability to evaluate the effect of variation in one parameter (including sampling strategy) on any other parameters incorporated into the implementation. While the final choice of project design is of course the user's discretion, these methods and systems let the user create a broad variety of "what if" scenarios, by which the correlation among different parameters can be examined.

In this sense, the concept of "parameter" or "degree of freedom" can be extended far beyond the actual synthesis step(s) to make the library. One skilled in the art will recognize that any part of the entire combinatorial process that can be quantified and varied can be thought of as a degree of freedom. Other degrees of freedom can include, but are not limited to, choice of tool, design of tool, design of substrate, number of substrates, environmental constraints, personnel requirements, total project timeline, or any number of other factors that may not typically be thought of as degrees of freedom in the compositional sense. By definition, these degrees of freedom can be adjusted, and typically their adjustment will have direct consequence on the behavior of one or more other parts of the system. Thus, it is important to understand how potential changes in one degree of freedom (e.g., tool design) affect all other degrees of freedom (e.g., personnel requirements).

As a simple example, consider a driver whose car breaks down by the side of the road. One repair solution might involve the driver attempting repair, while another solution could involve calling a repair expert. The best solution will depend on a variety of parameters, for example: skill of the driver at repair, ability to contact the repair expert, distance from the car to the repair expert, seriousness of problem, availability of tools to both driver or repair expert, time constraints, safety constraints, or any number of other parameters. The best solution to the problem requires an optimization of all available parameters and known data, and success can only be evaluated after having made and implemented a decision.

By extension, the resource cost of each experiment (site) in a combinatorial study can be a complex function of parameter space dimensionality and constraints on available resources: physical constraints, time deadlines, financial constraints, and other factors. For any of a plurality of ways to (for example) design tools, arrange experiments, perform synthesis processes, and make measurements, there is a broad possible variation in experimental "cost" per point. For a parameter space that is very large, it might be more cost effective to redesign an entire synthesis tool, or even build another tool altogether, rather than start immediately with an available tool. In this scenario, short term throughput is sacrificed (resources spent on tool redesign rather than synthesis) for long term throughput (in the long run, the integrated output of the improved tool design surpasses the first design). For smaller parameter spaces or coarser sampling strategies, the time and resource costs of tool redesign and manufacture might preclude significant tool redesign, but larger spaces requiring more experiments might ultimately benefit from redesign.

The relative importance of different parameters might be implemented as constraints in degrees of freedom. However, these constraints can be independently applied or adjusted as needed, and need not be the same for different implementations. While one implementation might require a given constraint (e.g., "the project must be completed in 3 months") another implementation might not require this constraint. Conversely, lack of adjustability in a given parameter can be easily implemented by removing that parameter from the model's implementation. As a result, simplified models can be implemented for systems requiring relatively few adjustable parameters. However, one skilled in the art will recognize that lack of any given adjustable parameter in one implementation does not preclude its incorporation in another implementation. The removal of one or any number of parameters from one implementation does not in any way preclude their addition for another implementation.

Examples of different implementation are briefly described below. These examples are by no means comprehensive. One skilled in the art will recognize that any implementation might contain more or fewer or the same parameters, that describe similar or other areas of any process. The following examples are loosely grouped according to the total available degrees of freedom of the system, described herein as "modes." For ease of comprehension, the modes are loosely ordered by increasing freedom. Thus, earlier modes represent fairly constrained systems, which can be construed as a project described as "make do with what's available, and find the best way." Later modes can be described as "change any combination of parameters to find the best way." Thus, system 100 can be configured to operate in multiple modes; the illustrative examples below only illustrate a few of these modes. For simplicity, the modes are largely described in terms of chemical composition space.

These modes can be generally exemplified as illustrated in FIG. 12. In general, optimization program 130 receives inputs including a set of sampling requirements 1210 for an N-dimensional space of parameters to be varied in a set of experiments and a set of resource constraints 1220 for resources (e.g., device 140) that will be used to perform the set of experiments. Based on these inputs, optimization program 130 identifies a set of experiments 1230 that is "fabricable" in the sense that it can be performed by (and subject to the constraints of) the resources.

In one mode of operation, as exemplified by method 700 described above, the sampling requirements include a target basket and the resource constraints include one or more device patterns, and optimization program 130 uses these inputs to determine an efficient design by which to create the target basket in light of the constraints defined for device 140. In this mode of operation, optimization program 130 is constrained to generate experiment designs that include the specified target basket compositions, and to do so using a particular pattern or patterns (e.g., representing a tool whose fundamental pattern is currently implemented. Adjustable parameters can include, e.g., the number of deposition steps, and similarity between composition of points on the library and desired basket composition. In this mode of operation, system 100 provides an efficient means to sample a desired space with a desired set of points using a particular tool design; obtaining a close match to the target basket takes some priority over synthesis process speed, subject to device constraints.

In a second mode of operation, the user might decide that the exact compositions in the desired basket are less important, provided the library creates a set of points that are reasonably close to a desired set of compositions. This mode can be described as one in which the boundaries of the parameter space are constrained (e.g., the library should consist of points containing Fe, Al, Ni, Co, and Si), and perhaps the sampling strategy is constrained (the points might sample the parameter space in some distributed fashion), but the composition of each site is unconstrained. In this mode, the sampling inputs 1210 can be considered to define an "approximate basket"—that is, an input specifying, for example, dimensionality, number of sample points, precision, and sampling characteristics for a basket, such as a minimum distance between points or a threshold distance from specified target points, but not specific compositions. Optimization program 130 uses this input, in combination with device patterns as discussed in the preceding paragraph, to determine an efficient library design that meets the approximate basket requirements. In contrast to the first mode, in this mode of operation, rapid processing takes priority over the requirement of exact duplication of a previously defined set of points in a target basket, again subject to device constraints. System 100 might then provide a synthesis strategy that is faster than that in the previous mode, but sacrifices exact compositional control over each site. One skilled in the art will recognize that this mode enables system 100 to perform a variety of pseudo-random sampling strategies, based on physical tool boundary conditions.

In a third mode, the sampling inputs 1210 define either a target basket or approximate basket as discussed above, and the constraint inputs include multiple patterns that represent alternate resource configurations (e.g., alternate designs of device 140). Optimization program 130 uses these inputs to generate efficient designs for both the set of experiments and the resources (e.g., a tool to prepare the library). In this mode of operation, library optimization program 130 attempts to identify both an optimal library design (including, for example, number of substrates) and an optimal pattern or set of patterns defining the tool, identifying a best combination of pattern attributes (e.g., shapes, sizes, number of patterns, etc.) that could yield a particularly efficient way to sample a given space. In this mode, rapid synthesis takes priority over both basket precision and tool constraints. Extensions of this mode can be used to evaluate the effect of fundamental, broad reaching variables on project outcome. For very large parameter spaces, the short term sacrifices incurred in "retooling" any given process step might be compensated for by a process that ultimately leads to success sooner.

Any number of other modes can be incorporated into an implementation. Possible parameters could include diversity in starting materials, downstream measurement requirements (e.g., one type of measurement requires a certain size sample), or any other adjustable part of the experimental process. As one example of the first of these, device 140 can be provided with a set of one or more libraries of materials to use as inputs in the design and preparation of a "daughter" library. In this implementation, each "parent" library—such as an array or matrix of wells as described above—preferably incorporates some chemical or any other diversity. Device 140 samples this diversity using, e.g., an array or matrix of liquid dispensing pipettes as is also described above. In addition to one or more of the inputs discussed above, in this implementation library optimization program 130 can also take as an input a component pattern derived from a combination of the pre-existing diversity in the parent libraries and the device pattern(s) imposed by device 140. Optimization of this system provides a means, e.g., to identify an optimum synthesis procedure for the preparation of a target library using a given set of parent libraries (e.g., selected from an existing archive of libraries), or an optimum set of such parent libraries (again, selected from a larger set of available libraries) that will yield an efficient synthesis of the target library (or an acceptable approximation thereof).

By extension, it is important to recognize that a broad variety of parameters can yield an improvement in PE. One fundamental way to increase PE for a process step is to use certain sites to mask other sites. This might be implemented by appropriately designing a tool, choosing substrate order, choosing experiment lattices, choosing application conditions, or choosing any number of other parameters, such that the function of masking a site from a given process is implemented by using another available site. In capturing the application of the process, one site simultaneously masks another site.

The methods and computer programs of the invention can be implemented, in whole or in part, in digital electronic circuitry, or in computer hardware, firmware, software, or in combinations of them. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

A number of implementations of the invention have been described. Nevertheless, it will be understood that various modifications may be made without departing from the spirit and scope of the invention. Accordingly, other embodiments are within the scope of the following claims.

What is claimed is:

1. A computer-implemented method of designing a set of experiments to be performed with a set of resources, the method comprising:

providing a set of parameters and a set of constraints, the parameters including a plurality of factors to be varied in a set of experiments and representing axes defining a parameter space, the set of constraints including one or more experimental constraints representing limitations on operations that can be performed with the set of resources;

generating a plurality of configurations based on the parameters and the experimental constraints, each configuration including a plurality of experimental points, each point having a set of values for the parameters;

selecting a configuration from the plurality of configurations; and defining a set of experiments based on the selected configuration.

2. The method of claim 1, wherein:

providing a set of constraints includes providing one or more experiment lattices, each experiment lattice including one or more lattice points and representing an arrangement in which experiments in a set of experiments will be performed.

3. The method of claim 2, wherein:

the lattice points represent locations on a substrate.

4. The method of claim 2, wherein:

providing a set of constraints includes providing a set of one or more patterns, the patterns representing the application of parameters to one or more lattice points of an experiment lattice under a set of experimental constraints, the experimental constraints for a given pattern being represented by a set of attributes; and generating a plurality of configurations includes:

a) generating a plurality of instances of one or more of the patterns, each pattern instance being defined by a set of attribute values for the attributes defining the pattern, the set of attribute values specifying a quantity of a parameter to be applied at one or more lattice points of an experiment lattice; and b) combining the pattern instances to generate a configuration, such that the parameter values for a point in the configuration are based on the parameter values specified by the combined pattern instances for a corresponding lattice location.

5. The method of claim 4, wherein:

the patterns include one or more device patterns having attributes representing constraints associated with one or more devices for performing operations at one or more locations represented by lattice points of the experiment lattice.

6. The method of claim 5, wherein:

the operations include process steps for applying parameters at the locations.

7. The method of claim 6, wherein:

the process steps include depositing materials at one or more locations.

8. The method of claim 6, wherein:

the process steps include subjecting materials at one or more locations to processing conditions.

9. The method of claim 5, wherein:

the device pattern attributes for one or more device patterns include one or more device geometry attributes specifying a geometry in which a parameter will be applied to a substrate.

10. The method of claim 9, wherein:

the device geometry attributes include a thickness attribute representing a quantity of the parameter to be applied.

11. The method of claim 5, wherein:

one or more of the device patterns represent openings in a mask for exposing locations on a substrate.

12. The method of claim 5, wherein:

one or more of the device patterns represent openings in a shutter mask system for exposing locations on a substrate.

13. The method of claim 5, wherein:

one or more of the device patterns represent a set of dispensing tips for delivering materials to locations on a substrate.

14. The method of claim 5, wherein:

the plurality of pattern instances includes a plurality of device pattern instances specifying amounts of one or more materials to be deposited at locations on a substrate.

15. The method of claim 4, wherein:

providing a set of constraints includes providing one or more component patterns representing an arrangement of materials to be used in performing a set of experiments; and generating a plurality of pattern instances includes superimposing the pattern instances with the component patterns, such that the pattern instances represent the application of the arrangement of materials to lattice points of the experiment lattice.

16. The method of claim 15, wherein:

the component patterns include a component pattern representing a library lattice for a parent library of materials to be used in performing a set of experiments.

17. The method of claim 15, wherein:

the one or more component patterns include a first component pattern representing a first arrangement of materials that could be used in performing the set of experiments and a second arrangement of materials that could be used in performing the set of experiments;

generating a plurality of configurations includes generating a first configuration based on the first component pattern and a second configuration based on the second component pattern; and selecting a configuration includes identifying an optimum component pattern from the first and second component patterns.

18. The method of claim 4, wherein:

combining the pattern instances includes superimposing a plurality of pattern instances with one or more experiment lattices.

19. The method of claim 4, wherein:

generating a plurality of configurations includes repeating the steps of generating a plurality of pattern instances and combining the pattern instances.

20. The method of claim 19, wherein:

generating a plurality of configurations includes generating a plurality of sets of pattern instances by varying the number and/or attribute values of pattern instances.

21. The method of claim 4, wherein:

generating a plurality of configurations includes generating a first configuration and subsequently generating a sequence of second configurations, each of the second configurations being generated by adding a pattern instance to a preceding configuration in the sequence, removing a pattern instance from a preceding configuration in the sequence, or changing an attribute value for an attribute of a pattern instance in a preceding configuration in the sequence.

22. The method of claim 21, wherein:

generating a first configuration includes generating a pseudo-random configuration.

23. The method of claim 4, wherein:

selecting an configuration from the plurality of configurations includes calculating a figure of merit for each of the configurations and applying a selection rule to the calculated figures of merit.

24. The method of claim 23, wherein:

calculating a figure of merit for a configuration includes comparing one or more of the parameter space points for the experimental configuration with a set of sampling requirements for a desired set of experiments.

25. The method of claim 24, wherein:

the set of sampling requirements includes a set of target points representing a desired set of experiments.

26. The method of claim 25, wherein:

the selected configuration is required to include a point corresponding to each point in the set of target points.

27. The method of claim 25, wherein:

the figure of merit for a configuration is calculated as a function of a distance in the parameter space between points in the configuration and points in the set of target points.

28. The method of claim 27, wherein:

the figure of merit for a configuration is further calculated as a function of the resource cost to perform a set of experiments defined by the experimental points in the configuration.

29. The method of claim 28, wherein:

the resource cost for a configuration is determined as a function of the number of patterns from which the configuration was generated.

30. The method of claim 4, wherein:

combining the pattern instances includes defining a sequence of pattern instances, the points in the configuration being defined in part by order information derived from the sequence.

31. The method of claim 30, wherein:

generating a plurality of configurations includes generating a first configuration and subsequently generating a sequence of second configurations, each of the second configurations being generated by adding a pattern instance to a preceding configuration in the sequence, removing a pattern instance from a preceding configuration in the sequence, changing an attribute value for an attribute of a pattern instance in a preceding configuration in the sequence, or changing the position of a pattern instance in the sequence.

32. The method of claim 30, wherein:

selecting a configuration includes identifying an optimum sequence of events for the set of experiments.

33. The method of claim 4, wherein:

the set of patterns includes patterns representing alternate applications of parameters to lattice points of an experiment lattice, the set of patterns including a first pattern defined by a first set of attributes and a second pattern defined by a second set of attributes, the second set of attributes differing from the first set of attributes in at least one attribute;

generating a plurality of configurations includes combining instances of the first pattern to generate a first configuration and combining instances of the second pattern to generate a second configuration; and selecting a configuration includes identifying an optimum pattern from the first and second patterns.

34. The method of claim 4, wherein:

the one or more experiment lattices include a first experiment lattice representing a first arrangement in which a set experiments could be performed and a second experiment lattice representing a second arrangement in which the set of experiments could be performed;

generating a plurality of configurations includes superimposing pattern instances with the first experiment lattice to generate a first configuration and superimposing pattern instances with the second experiment lattice to generate a second configuration;and selecting a configuration includes identifying an optimum experiment lattice from the first and second experiment lattices.

35. The method of claimed 1, wherein:
each configuration in the plurality of configurations represents a set of experiments that can be preformed with the set of resources.

36. The method of claim 1, wherein:
generating a plurality of configurations and selecting a configuration includes performing an optimization process.

37. The method of claim 36, wherein:
the optimization process is selected from the group consisting of Monte Carlo processes, simplex processes, conjugate gradient processes and genetic algorithm processes.

38. The method of claim 36, wherein:
performing an optimization process includes performing a Monte Carlo optimization process based on simulated annealing, parallel tempering, or a combination thereof.

39. The method of claim 1, wherein:
defining the set of experiments based on the selected configuration includes introducing a change to the selected configuration and defining the set of experiments based on the changed configuration.

40. The method of claim 1, further comprising:
outputting electronic data representing a design for the set of experiments.

41. The method of claim 1, wherein:
the set of constraints includes a first set of experimental constraints representing limitations on operations that can be performed with a first set of resources and a second set of experimental constraints representing limitations on operations that can be performed with a second set of resources; and
generating a plurality of configurations includes generating a first configuration based on the first set of experimental constraints and a second configuration based on the second set of experimental constraints; and
selecting a configuration includes identifying an optimum set of resources from the first and second sets of resources.

42. A computer-implemented method of designing a set of experiments to be performed with a set of resources, the method comprising:
providing a set of parameters, one or more experiment lattices, and one or more patterns, the parameters including a plurality of factors to be varied in a set of experiments and representing axes defining a parameter space, each experiment lattice including one or more lattice points and representing an arrangement in which experiments in a set of experiments will be performed, and each pattern representing the application of a parameter to one or more lattice points of an experiment lattice under a set of experimental constraints representing limitations on operations that can be performed with the set of resources, the experimental constraints for a given pattern being represented by a set of attributes;
generating a plurality of instances of one or more of the patterns, each pattern instance being defined by a set of attribute values for the attributes defining the pattern, the set of attribute values specifying a quantity of a parameter to be applied at one or more lattice points of an experiment lattice;
combining the pattern instances to generate a set of experimental points, each point having a set of values for the parameters, the parameter values for a point in the configuration being based on the parameter values specified by the combined pattern instances for a corresponding lattice location; and
defining a set of experiments based on the experimental points.

43. A computer-implemented method of designing a set of experiments to be performed with a set of resources, the method comprising:
providing a set of parameters and a set of constraints, the parameters including a plurality of factors to be varied in a set of experiments and representing axes defining a parameter space, the set of constraints including a set of target points representing a desired set of experiments, one or more experiment lattices and one or more patterns, each of the set of target points having a set of parameters values defining a position in the parameter space, each experiment lattice including one or more lattice points and representing an arrangement in which experiments in a set of experiments will be performed, the patterns representing the application of parameters to one or more lattice points of an experiment lattice under a set of experimental constraints representing limitations on operations that can be performed with the set of resources, the experimental constraints for a given pattern being represented by a set of attributes;
generating a plurality of configurations based on the parameters and the constraints, each configuration including a plurality of experimental points, each point having a set of values for the parameters, each configuration being generated by:
a) generating a plurality of instances of one or more of the patterns, each pattern instance being defined by a set of attribute values for the attributes defining the pattern, the set of attribute values specifying a quantity of a parameter to be applied at one or more lattice points of an experiment lattice; and
b) combining the pattern instances to generate a configuration, such that the parameter values for a point in the configuration are based on the parameter values specified by the combined pattern instances for a corresponding lattice location, each configuration including a plurality of experimental points, each point having a set of values for the parameters;
comparing the experimental points of the configurations to the set of target points;
selecting a configuration from the plurality of configurations based on the comparing; and
defining a set of experiments based on the selected configuration.

44. A computer-implemented method of designing a set of experiments to be performed with a set of resources, the method comprising:
providing a set of parameters and a set of constraints, the parameters including a plurality of factors to be varied in a set of experiments and representing axes defining a parameter space, the set of constraints including a set of target points representing a desired set of experiments, one or more experiment lattices and a plurality of patterns, each of the set of target points having a set if parameters values defining a position in the parameter space, each experiment lattice including one or more lattice points and representing an arrangement in which experiments in a set of experiments will be performed, the patterns representing alternate applications of parameters to lattice points of an experiment lattice under sets of experimental constraints representing limitations on operations that can be performed with the set of resources, the experimental constraints for a given pattern being represented by a set of attributes, the set of patterns including a first pattern defined by a first set of attributes and a second pattern defined by a second set of attributes, the second set of attributes differing from the first set of attributes in at least one attribute;

generating a plurality of configurations based on the parameters and the constraints, each configuration including a plurality of experimental points, each point having a set of values for the parameters, each configuration being generated by:

a) generating a plurality of instances of one or more of the patterns, each pattern instance being defined by a set of attribute values for the attributes defining the pattern, the set of attribute values specifying a quantity of a parameter to be applied at one or more lattice points of an experiment lattice; and b) combining the pattern instances to generate a configuration, such that the parameter values for a point in the configuration are based on the parameter values specified by the combined pattern instances for a corresponding lattice location, each configuration including a plurality of experimental points, each point having a set of values for the parameters;

comparing the experimental points of the configurations to the set of target points;

selecting a configuration from the plurality of configurations based on the comparing; and defining a set of experiments based on the selected configuration;

wherein the plurality of configurations includes one or more first configurations generated by combining instances of the first pattern and one or more second configurations generated by combining instances of the second pattern, and selecting a configuration includes identifying an optimum pattern from the first and second patterns.

45. A computer program product on a computer-readable medium for designing a set of experiments to be performed with a set of resources, the program comprising instructions operable to cause a programmable processor to:

provide a set of parameters and a set of constraints, the parameters including a plurality of factors to be varied in a set of experiments and representing axes defining a parameter space, the set of constraints including one or more experimental constraints representing limitations on operations that can be performed with the set of resources;

generate a plurality of configurations based on the parameters and the constraints, each configuration including a plurality of experimental points, each point having a set of values for the parameters;

select a configuration from the plurality of configurations; and define a set of experiments based on the selected configuration.

46. The computer program product of claim 45, wherein: the set of constraints defines one or more experiment lattices, each experiment lattice including one or more lattice points and representing an arrangement in which experiments in a set of experiments will be performed.

47. The computer program product of claim 46, wherein: the lattice points represent locations on a substrate.

48. The computer program product of claim 46, wherein: the set of constraints defines a set of one or more patterns, the patterns representing the application of parameters to one or more lattice points of an experiment lattice under a set of experimental constraints, the experimental constraints for a given pattern being represented by a set of attributes; and the instructions operable to cause a programmable processor to generate a plurality of configurations include instructions operable to cause a programmable processor to:

a) generate a plurality of instances of one or more of the patterns, each pattern instance being defined by a set of attribute values for the attributes defining the pattern, the set of attribute values specifying a quantity of a parameter to be applied at one or more lattice points of an experiment lattice; and b) combine the pattern instances to generate a configuration, such that the parameter values for a point in the configuration are based on the parameter values specified by the combined pattern instances for a corresponding lattice location.

49. The computer program product of claim 48, wherein: the patterns include one or more device patterns having attributes representing constraints associated with one or more devices for performing operations at one or more locations represented by lattice points of the experiment lattice.

50. The computer program product of claim 49, wherein: the operations include process steps for applying parameters at the locations.

51. The computer program product of claim 50, wherein: the process steps include depositing materials at one or more locations.

52. The computer program product of claim 50, wherein: the process steps include subjecting materials at one or more locations to processing conditions.

53. The computer program product of claim 49, wherein: the device pattern attributes for one or more device patterns include one or more device geometry attributes specifying a geometry in which a parameter will be applied to a substrate.

54. The computer program product of claim 53, wherein: the device geometry attributes include a thickness attribute representing a quantity of the parameter to be applied.

55. The computer program product of claim 49, wherein: one or more of the device patterns represent openings in a mask for exposing locations on a substrate.

56. The computer program product of claim 49, wherein: one or more of the device patterns represent openings in a shutter mask system for exposing locations on a substrate.

57. The computer program product of claim 49, wherein: one or more of the device patterns represent a set of dispensing tips for delivering materials to locations on a substrate.

58. The computer program product of claim 49, wherein: the plurality of pattern instances includes a plurality of device pattern instances specifying amounts of one or more materials to be deposited at locations on a substrate.

59. The computer program product of claim 48, wherein:

the set of constraints defines one or more component patterns representing an arrangement of materials to be used in performing a set of experiments; and the instructions operable to cause a programmable processor to generate a plurality of pattern instances include instructions operable to cause a programmable processor to superimpose the pattern instances with the component patterns, such that the pattern instances represent the application of the arrangement of materials to lattice points of the experiment lattice.

60. The computer program product of claim 59, wherein:

the component patterns include a component pattern representing a library lattice for a parent library of materials to be used in performing a set of experiments.

61. The computer program product of claim 59, wherein:

the one or more component patterns include a first component pattern representing a first arrangement of materials that could be used in performing the set of experiments and a second arrangement of materials that could be used in performing the set of experiments;

the instructions operable to cause a programmable processor to generate a plurality of configurations include instructions operable to cause a programmable processor to generate a first configuration based on the first component pattern and a second configuration based on the second component pattern; and the instructions operable to cause a programmable processor to select a configuration include instructions operable to cause a programmable processor to identify an optimum component pattern from the first and second component patterns.

62. The computer program product of claim 48, wherein:

the instructions operable to cause a programmable processor to combine the pattern instances include instructions operable to cause the programmable processor to superimpose a plurality of pattern instances with one or more experiment lattices.

63. The computer program product of claim 48, wherein:

the instructions operable to cause a programmable processor to generate a plurality of configurations include instructions operable to cause a programmable processor to repeat the steps of generating a plurality of pattern instances and combining the pattern instances.

64. The computer program product of claim 63, wherein:

the instructions operable to cause a programmable processor to generate a plurality of configurations include instructions operable to cause a programmable processor to generate a plurality of sets of pattern instances by varying the number and/or attribute values of pattern instances.

65. The computer program product of claim 48, wherein:

the instructions operable to cause a programmable processor to generate a plurality of configurations include instructions operable to cause a programmable processor to generate a first configuration and subsequently generate a sequence of second configurations, each of the second configurations being generated by adding a pattern instance to a preceding configuration in the sequence, removing a pattern instance from a preceding configuration in the sequence, or changing an attribute value for an attribute of a pattern instance in a preceding configuration in the sequence.

66. The computer program product of claim 65, wherein:

the first configuration includes a pseudo-random configuration.

67. The computer program product of claim 48, wherein:

the instructions operable to cause a programmable processor to select an configuration from the plurality of configurations include instructions operable to cause a programmable processor to calculate a figure of merit for each of the configurations and apply a selection rule to the calculated figures of merit.

68. The computer program product of claim 67, wherein:

the instructions operable to cause a programmable processor to calculate a figure of merit for a configuration include instructions operable to cause a programmable processor to compare one or more of the parameter space points for the experimental configuration with a set of sampling requirements for a desired set of experiments.

69. The computer program product of claim 68, wherein:

the set of sampling requirements includes a set of target points representing a desired set of experiments.

70. The computer program product of claim 69, wherein:

the selected configuration is required to include a point corresponding to each point in the set of target points.

71. The computer program product of claim 69, wherein:

the figure of merit for a configuration is calculated as a function of a distance in the parameter space between points in the configuration and points in the set of target points.

72. The computer program product of claim 71, wherein:

the figure of merit for a configuration is further calculated as a function of the resource cost to perform a set of experiments defined by the experimental points in the configuration.

73. The computer program product of claim 72, wherein:

the resource cost for a configuration is determined as a function of the number of patterns from which the configuration was generated.

74. The computer product of claim 48, wherein the instructions operable to cause a programmable processor to combine the pattern instances include instructions operable to cause a programmable processor to define a sequence of pattern instances, the points in the configuration being defined in part by order information derived from the sequence.

75. The computer program product of claim 74, wherein:

the instructions operable to cause a programmable processor to generate a plurality of configurations include instructions operable to cause a programmable processor to generate a first configuration and subsequently generate a sequence of second configurations, each of the second configurations being generated by adding a pattern instance to a preceding configuration in the sequence, removing a pattern instance from a preceding configuration in the sequence, changing an attribute value, for an attribute of a pattern instance in a preceding configuration in the sequence, or changing the position of a pattern instance in the sequence.

76. The computer program product of claim 74, wherein:

the instructions operable to cause a programmable processor to select a configuration include instructions operable to cause a programmable processor to identify an optimum sequence of events for the set of experiments.

77. The computer program product of claim 48, wherein:

the set of patterns includes patterns representing alternate applications of parameters to lattice points of an experiment lattice, the set of patterns including a first pattern defined by a first set of attributes and a second pattern defined by a second set of attributes, the second set of attributes differing from the first set of attributes in at least one attribute;

the instructions operable to cause a programmable processor to generate a plurality of configurations include instructions operable to cause a programmable processor to combine instances of the first pattern to generate a first configuration and combine instances of the second pattern to generate a second configuration; and the instructions operable to cause a programmable processor to select a configuration include instructions operable to cause a programmable processor to identify an optimum pattern from the first and second patterns.

78. The computer program product of claim 48, wherein:

the one or more experiment lattices include a first experiment lattice representing a first arrangement in which a set of experiments could be performed and a second experiment lattice representing a second arrangement in which the set of experiments could be performed;

the instructions operable to cause a programmable processor to generate a plurality of configurations include instructions operable to cause a programmable processor to superimpose pattern instances with the first experiment lattice to generate a first configuration and superimpose pattern instances with the second experiment lattice to generate a second configuration; and the instructions operable to cause a programmable processor to select a configuration include instructions operable to cause a programmable processor to identify an optimum experiment lattice from the first and second experiment lattices.

79. The computer program product of claim 45, wherein: each configuration in the plurality of configurations represents a set of experiments capable of being performed with the set of resources.

80. The computer program product of claim 45, wherein: the instructions operable to cause a programmable processor to generate a plurality of configurations and select a configuration include instructions operable to cause a programmable processor to perform an optimization process.

81. The computer program product of claim 80, wherein: the optimization process is selected from the group consisting of Monte Carlo processes, simplex processes, conjugate gradient processes and genetic algorithm processes.

82. The computer program product of claim 80, wherein: the optimization process includes a Monte Carlo optimization process based on simulated annealing, parallel tempering, or a combination thereof.

83. The computer program product of claim 45, wherein: the instructions operable to cause a programmable processor to define the set of experiments based on the selected configuration include instructions operable to cause a programmable processor to introduce a change to the selected configuration and define the set of experiments based on the changed configuration.

84. The compute program product of claim 45, further comprising instructions operable to cause a programmable processor to:

output electronic data representing a design for the set of experiments.

85. The computer program product of claim 45, wherein: the set of constraints includes a first set of experimental constraints representing limitations on operations that can be performed with a first set of resources and a second set of experimental constraints representing limitations on operations that can be performed with a second set of resources;

the instructions operable to cause a programmable processor to generate a plurality of configurations include instructions operable to cause a programmable processor to generate a first configuration based on the first set of experimental constraints and a second configuration based on the second set of experimental constraints; and the instructions operable to cause a programmable processor to select a configuration include instructions operable to cause a programmable processor to identify an optimum set of resources from the first and second sets of resources.

86. A computer program product on a computer-readable medium for designing a set of experiments to be performed with a set of resources, the program comprising instructions operable to cause a programmable processor to provide a set of parameters, one or more experiment lattices, and one or more patterns, the parameters including a plurality of factors to be varied in a set of experiments and representing axes defining a parameter space, each experiment lattice including one or more lattice points and representing an arrangement in which experiments in a set of experiments will be performed, and each pattern representing the application of a parameter to one or more lattice points of an experiment lattice under a set of experimental constraints representing limitations on operations that can be performed with the set of resources, the experimental constraints for a given pattern being represented by a set of attributes;

generate a plurality of instances of one or more of the patterns, each pattern instance being defined by a set of attribute values for the attributes defining the pattern, the set of attribute values specifying a quantity of a parameter to be applied at one or more lattice points of an experiment lattice; and combine the pattern instances to generate a set of experimental points, each point having a set of values for the parameters, the parameter values for a point in the configuration being based on the parameter values specified by the combined pattern instances for a corresponding lattice location; and define a set of experiments based on the experimental points.

87. A system for performing a set of experiments, the system comprising:

one or more devices configured to apply a plurality of parameters to a plurality of locations on a substrate, the parameters including a plurality of factors to be varied in a set of experiments and representing axes defining a parameter space, the application of parameters to the substrate locations being defined by one or more patterns, each pattern representing the application of a parameter to one or more substrate locations under a set of experimental constraints representing limitations on operations that can be performed with the devices, the experimental constraints for a given pattern being represented by a set of attributes; and a programmable processor configured to:

a) generate a plurality of instances of one or more of the patterns, each pattern instance being defined by a set of attribute values for the attributes defining the pattern, the set of attribute values specifying a quantity of the parameter to be applied at one or more locations on the substrate;

b) combine the pattern instances to generate a configuration, each configuration including a plurality of experimental points, each point having a set of values for the parameters, the parameter values for a point in the configuration being based on the quantities specified by the combined pattern instances for a corresponding substrate location;

c) define a design for a set of experiments based on the configuration, the design including for each experiment in the set of experiments a set of parameter values quantifying each of a plurality of the parameters to be applied in the experiment; and d) instruct the devices to carry out the set of experiments according to the design.

88. The system of claim 87, wherein the programmable processor is further configured to:

provide a set of target points representing a desired set of experiments, the set of target points including a plurality of points in a parameter space defined by a plurality of experimental parameters, each of the points in the set of target points having a set of parameter values;

generate a plurality of configurations by generating a plurality of sets of pattern instances and combining the instances of each set of the pattern instances to generate an configuration, each configuration including a plurality of points in the parameter space, each of the plurality of points in the configuration having a set of parameter values;

select an configuration from the plurality of experimental configurations based on a comparison of the points in the configurations to the set of target points; and define the design for the set of experiments based on the points in the selected configuration.

89. A computer-implemented method of designing a set of experiments to be performed with a set of resources, the method comprising:

providing a set of parameters and a set of constraints, the parameters including a plurality of factors to be varied in a set of experiments and representing axes defining a parameter space, the set of constraints including a set of sampling requirements for a set of experiments, one or more experiment lattices and one or more patterns, each experiment lattice including one or more lattice points and representing an arrangement in which experiments in a set of experiments will be performed, the patterns representing the application of parameters to one or more lattice points of an experiment lattice under a set of experimental constraints representing limitations on operations that can be performed with the set of resources, the experimental constraints for a given pattern being represented by a set of attributes;

generating a plurality of configurations based on the parameters and the constraints, each configuration including a plurality of experimental points, each point having a set of values for the parameters, each configuration being generated by:

a) generating a plurality of instances of one or more of the patterns, each pattern instance being defined by a set of attribute values for the attributes defining the pattern, the set of attribute values specifying a quantity of a parameter to be applied at one or more lattice points of an experiment lattice; and b) combining the pattern instances to generate a configuration, such that the parameter values for a point in the configuration are based on the parameter values specified by the combined pattern instances for a corresponding lattice location, each configuration including a plurality of experimental points, each point having a set of values for the parameters;

comparing the experimental points of the configurations to the set of sampling requirements;

selecting a configuration from the plurality of configurations based on the comparing; and defining a set of experiments based on the selected configuration.

90. The method of claim 89, wherein:

the set of sampling requirements specifies one or more of a number of sample points, a sampling precision, or a threshold distance from a set of target points.

91. A computer-implemented method of designing a set of experiments to be performed with a set of resources, the method comprising:

providing a set of parameters and a set of constraints, the parameters including a plurality of factors to be varied in a set of experiments and representing axes defining a parameter space, the set of constraints including a set of sampling requirements for a set of experiments, one or more experiment lattices and a plurality of patterns, each experiment lattice including one or more lattice points and representing an arrangement in which experiments in a set of experiments will be performed, the patterns representing alternate applications of parameters to lattice points of an experiment lattice under sets of experimental constraints representing limitations on operations that can be performed with the set of resources, the experimental constraints for a given pattern being represented by a set of attributes, the set of patterns including a first pattern defined by a first set of attributes and a second pattern defined by a second set of attributes, the second set of attributes differing from the first set of attributes in at least one attribute;

generating a plurality of configurations based on the parameters and the constraints, each configuration including a plurality of experimental points, each point having a set of values for the parameters, each configuration being generated by:

a) generating a plurality of instances of one or more of the patterns, each pattern instance being defined by a set of attribute values for the attributes defining the pattern, the set of attribute values specifying a quantity of a parameter to be applied at one or more lattice points of an experiment lattice; and b) combining the pattern instances to generate a configuration, such that the parameter values for a point in the configuration are based on the parameter values specified by the combined pattern instances for a corresponding lattice location, each configuration including a plurality of experimental points, each point having a set of values for the parameters;

comparing the experimental points of the configurations to the set of sampling requirements;

selecting a configuration from the plurality of configurations based on the comparing; and defining a set of experiments based on the selected configuration;

wherein the plurality of configurations includes one or more first configurations generated by combining instances of the first pattern and one or more second configurations generated by combining instances of the second pattern, and selecting a configuration includes identifying an optimum pattern from the first and second patterns.

92. A computer-implemented method of generating a design for a library of materials to be prepared with a set of resources, the method comprising:

providing a set of parameters and a set of constraints, the parameters including a plurality of factors to be varied during preparation of the library of materials and representing axes defining a parameter space, the set of constraints including one or more experiment lattices, each experiment lattice including one or more lattice points and representing one or more substrates on which the library of materials is to be prepared, the set of constraints also including one or more experimental constraints representing limitations on operations that can be performed with the set of resources;

generating a plurality of configurations based on the parameters and the experimental constraints, each configuration including a plurality of points, each point having a set of values for the parameters and being assigned to a lattice point of an experiment lattice;

selecting a configuration from the plurality of configurations; and generating a library design based on the selected configuration, the library design including a plurality of points, each point representing a material to be included in the library of materials and having a set of values for the parameters, the set of values being derived from the values for the selected configuration.

93. The method of claim 92, wherein:

providing a set of constraints includes providing a set of one or more patterns, the patterns representing the application of parameters to one or more lattice points of an experiment lattice under a set of experimental constraints, the experimental constraints for a given pattern being represented by a set of attributes; and generating a plurality of configurations includes:

a) generating a plurality of instances of one or more of the patterns, each pattern instance being defined by a set of attribute values for the attributes defining the pattern, the set of attribute values specifying a quantity of a parameter to be applied at one or more lattice points of an experiment lattice; and b) combining the pattern instances to generate a configuration, such that the parameter values for a point in the configuration are based on the parameter values specified by the combined pattern instances for a corresponding lattice location.

94. A computer program product on a computer-readable medium for designing a set of experiments to be performed with a set of resources, the program comprising instructions operable to cause a programmable processor to:

provide a set of parameters and a set of constraints, the parameters including a plurality of factors to be varied during preparation of the library of materials and representing axes defining a parameter space, the set of constraints including one or more experiment lattices, each experiment lattice including one or more lattice points and representing one or more substrates on which the library of materials is to be prepared, the set of constraints also including one or more experimental constraints representing limitations on operations that can be performed with the set of resources;

generate a plurality of configurations based on the parameters and the experimental constraints, each configuration including a plurality of points, each point having a set of values for the parameters and being assigned to a lattice point of an experiment lattice;

select a configuration from the plurality of configurations; and generate a library design based on the selected configuration, the library design including a plurality of points, each point representing a material to be included in the library of materials and having a set of values for the parameters, the set of values being derived from the values for the selected configuration.

95. The computer program product of claim 94, wherein:

the set of constraints includes a set of one or more patterns, the patterns representing the application of parameters to one or more lattice points of an experiment lattice under a set of experimental constraints, the experimental constraints for a given pattern being represented by a set of attributes; and the instructions operable to cause a programmable processor to generate a plurality of configurations include instructions operable to cause a programmable processor to:

a) generate a plurality of instances of one or more of the patterns, each pattern instance being defined by a set of attribute values for the attributes defining the pattern, the set of attribute values specifying a quantity of a parameter to be applied at one or more lattice points of an experiment lattice; and b) combine the pattern instances to generate a configuration, such that the parameter values for a point in the configuration are based on the parameter values specified by the combined pattern instances for a corresponding lattice location.

* * * * *

UNITED STATES PATENT AND TRADEMARK OFFICE
CERTIFICATE OF CORRECTION

PATENT NO.        : 6,996,550 B2
APPLICATION NO. : 10/024649
DATED             : February 7, 2006
INVENTOR(S)       : Wang et al.

It is certified that error appears in the above-identified patent and that said Letters Patent is hereby corrected as shown below:

Col. 40, Line 56, insert --of-- between "set" and "experiments"

Col. 40, Line 64, insert a space between ";" and "and"

Col. 46, Line 55, delete "," between "value" and "for"

Signed and Sealed this

Fifteenth Day of August, 2006

JON W. DUDAS
*Director of the United States Patent and Trademark Office*